United States Patent
Smiricinschi et al.

(10) Patent No.: US 11,328,413 B2
(45) Date of Patent: May 10, 2022

(54) SYSTEMS AND METHODS FOR ANALYTICAL DETECTION OF ANEURYSMS

(71) Applicant: iSchemaView, Inc., Menlo Park, CA (US)

(72) Inventors: Val Smiricinschi, Scottsdale, AZ (US); Kristen Catherine Karman-Shoemake, Fort Worth, TX (US); Mohamed Haithem Babiker, Phoenix, AZ (US)

(73) Assignee: iSchemaView, Inc., Menlo Park, CA (US)

( * ) Notice: Subject to any disclaimer, the term of this patent is extended or adjusted under 35 U.S.C. 154(b) by 42 days.

(21) Appl. No.: 16/516,136

(22) Filed: Jul. 18, 2019

(65) Prior Publication Data

US 2021/0019879 A1     Jan. 21, 2021

(51) Int. Cl.
*G06K 9/00* (2006.01)
*G06T 7/00* (2017.01)
*G06T 7/50* (2017.01)
*G06T 7/11* (2017.01)
*A61B 5/02* (2006.01)

(52) U.S. Cl.
CPC ........ *G06T 7/0012* (2013.01); *A61B 5/02014* (2013.01); *G06T 7/11* (2017.01); *G06T 7/50* (2017.01); *G06T 2207/20044* (2013.01); *G06T 2207/20072* (2013.01); *G06T 2207/30101* (2013.01)

(58) Field of Classification Search
None
See application file for complete search history.

(56) References Cited

U.S. PATENT DOCUMENTS

| | | | |
|---|---|---|---|
| 7,371,076 B2 | 5/2008 | Anderson et al. | |
| 7,742,629 B2 | 6/2010 | Zarkh et al. | |
| 7,986,822 B2 | 7/2011 | Hall et al. | |
| 8,781,194 B2 | 7/2014 | Malek et al. | |

(Continued)

FOREIGN PATENT DOCUMENTS

| | | |
|---|---|---|
| EP | 1469778 B1 | 9/2011 |
| EP | 2749222 | 7/2014 |

(Continued)

OTHER PUBLICATIONS

Yang et al., "Computer-aided detection of intracranial aneurysms in MR angiography", Journal of Digital Imaging, vol. 24, No. 1, Feb. 2011 (Year: 2011).*

(Continued)

*Primary Examiner* — Soo Jin Park
(74) *Attorney, Agent, or Firm* — Knobbe, Martens, Olson & Bear, LLP

(57) ABSTRACT

Systems and methods for detecting an aneurysm are disclosed. The method includes forming a virtual skeleton model. The virtual skeleton model has a plurality of edges with each edge having a plurality of skeleton points. Each skeleton point is associated with a subset of the plurality of blood vessel surface points. The method includes virtually fitting elliptically shaped tubules for each edge of the virtual skeleton model and identifying a potential aneurysm based on the fitted elliptically shaped tubules.

20 Claims, 31 Drawing Sheets

(56) References Cited

U.S. PATENT DOCUMENTS

| | | | |
|---|---|---|---|
| 10,290,230 | B2 | 5/2019 | Babiker et al. |
| 2005/0147297 | A1 | 7/2005 | McLaughlin et al. |
| 2006/0280351 | A1 | 2/2006 | Cotin et al. |
| 2006/0235669 | A1 | 10/2006 | Charbel et al. |
| 2008/0020362 | A1 | 1/2008 | Cotin et al. |
| 2008/0249755 | A1 | 10/2008 | Tek et al. |
| 2008/0262341 | A1 | 10/2008 | Boyden et al. |
| 2009/0214097 | A1 | 8/2009 | Mohamed et al. |
| 2010/0189333 | A1* | 7/2010 | Beck .......................... G06T 7/33 382/131 |
| 2012/0041318 | A1 | 2/2012 | Taylor |
| 2012/0321169 | A1 | 12/2012 | Baloch et al. |
| 2012/0323547 | A1 | 12/2012 | Balcoh et al. |
| 2013/0051640 | A1 | 2/2013 | Yu et al. |
| 2015/0127031 | A1 | 5/2015 | Yagi et al. |
| 2016/0203288 | A1 | 7/2016 | Meng et al. |
| 2019/0030368 | A1 | 1/2019 | Lipani |
| 2020/0352542 | A1 | 11/2020 | Errico et al. |

FOREIGN PATENT DOCUMENTS

| | | |
|---|---|---|
| EP | 3025638 | 6/2016 |
| JP | 2006-048247 | 2/2006 |
| WO | WO 2004/051604 | 6/2004 |
| WO | WO 2006/020792 | 2/2006 |
| WO | WO 2011/008906 A1 | 1/2011 |

OTHER PUBLICATIONS

Babiker et al. "Finite element modeling of embolic coil deployment: Multifactor characterization of treatment effects on cerebral aneurysm hemodynamics." Journal of Biomechanics 46 (2013) 2809-2816.

Babiker et al. "Investigation of the Influence of Coil Configuration on Cerebral Aneurysm Fluid Dynamics Using a Finite Element Approach." Poster 2013.

Babiker et al. "Preoperative simulation of endovascular treatment for cerebral aneurysms." Neuro News. Aug. 2012.

Babiker et al. "Influence of stent configuration on cerebral aneurysm fluid dynamics." Journal of Biomechanics, vol. 45:440-447, 2012.

Dequidt et al. "Interactive simulation of embolization coils: modeling and experimental validation." Medical Image Computing and Computer Assisted Intervention—MICCAI 2008:11th Intl. Conference, New York, NY; pp. 695-702.

Fluent Gambit Introduction and General Information (Mar. 24, 2008).

Gundert et al. "A rapid and computationally inexpensive method to virtually implant current and next-generation stents into subject-specific computational fluid dynamics models." Annals of Biomedical Eng., vol. 39(5):1423-1437, 2011.

Heller et al. "Crescent sign on magnetic resonance angiography revealing incomplete stent apposition: correlation with diffusion-weighted changes in stent-mediated coil embolization of aneurysms." J Neurosurg 115:624-632, 2011.

Hung et al. "Selective use of electrolytic detachable and fibered coils to embolize a wide-neck giant splenic artery pseudoaneurysm." Journal of Vascular Surgery. May 2005. pp. 889-892.

Kakalis et al. "The haemodynamics of endovascular aneurysm treatment: a computational modelling approach for estimating the influence of multiple coil deployment." IEEE Transactions on Medical Imaging, vol. 27(6):814-824, .2008.

Lubicz et al. "Selective Endovascular Treatment of Intracranial Aneurysms with Sapphire Coils." AJNR Am J Neuroradiol 25:1368-1372, Sep. 2004.

Ma et al. "Computer modeling of deployment and mechanical expansion of neurovascular flow diverter in patent-specific intracranial aneurysms." Journal of Biomechanics, vol. 45:2256-2263, 2012.

Rossitti, MD, et al. "Vascular dimensions of the cerebral arteries follow the principle of minimum work."

Tagliasacchi, et al. "Mean curvature skeletons." Computer Graphics Forum (Proceedings of the Symposium on Geometry Processing), 31(5):1735-1744, 2012.

Wakhloo et al. "Advances in Interventional Neuroradiology." Stroke, 2009; 40:e305-e312; originally published online Apr. 9, 2009. Downloaded from http://stroke.ahajournal.org on Apr. 3, 2014.

White et al. "Coils in a Nutshell: A Review of Coil Physical Properties." AJNR 29. Aug. 2008. pp. 1242-1246.

Boskamp et al. "Geometrical and Structural Analysis of Vessel Systems in 3D Medical Image Datasets," In: "vol. 5: Methods in Cardiovascular and Brain Systems." *World Scientific Publishing Co. Pte. Ltd.*, Jan. 1, 2005, pp. 1-60.

Lorigo et al. "Co-Dimension 2 Geodesic Active Contours for MRA Segmentation." Electronic Publishing, Artistic Imaging, and Digital Typography, *Lecture Notes in Computer Science*, Jan. 1, 1999, vol. 1613, pp. 126-139.

Czajkowska et al., "Skeleton Graph Matching vs. Maximum Weight Cliques aorta registration techniques", Computerized Medical Imaging and Graphics, Pergamon Press, New York, US, May 21, 2015, vol. 46, pp. 142-152.

Extended European Search Report in EP Application No. 20187432.8, dated Nov. 23, 2020.

Extended European Search Report in EP Application No. 20186459.2, dated Dec. 3, 2020.

Extended European Search Report in EP Application No. 20186463.4, dated Dec. 3, 2020.

Extended European Search Report in EP Application No. 20186457.6, dated Dec. 9, 2020.

International Search Report and Written Opinion issued in International Application No. PCT/US2015/012941 dated Apr. 24, 2015.

Jedwab et al., "A Study of the Geometrical and Mechanical Properties of a Self-Expanding Metallic Stent-Theory and Experiment" Journal of Applied Biomaterials, John Wiley & Sons, Inc., Jan. 1, 1993, vol. 4, pp. 77-85.

Matl et al., "Vascular image registration techniques: A living review", Medical Image Analysis, Jan. 1, 2017, vol. 35, pp. 1-17.

Mclaughlin et al., "Intensity-based Registration versus Feature-based Registration for Neuroinventions", Proc. Med. Image Underst. Anal., Jan. 1, 2001, pp. 1-4 Retrieved from the Internet: URL:https://www.researchgate.net/profile/Kawal_Rhode/publication/246495245_Intensity-based_Registration_versus_Feature-based_Registration_for_Neurointerventions/links/551290d80cf20bfdad51820e.pdf [retrieved on Nov. 20, 2020].

Mohamed et al., "Computer-aided planning for endovascular treatment of intracranial aneurysms (CAPETA)", Proceedings of SPIE, vol. 7625, Mar. 4, 2010, p. 762532.

\* cited by examiner

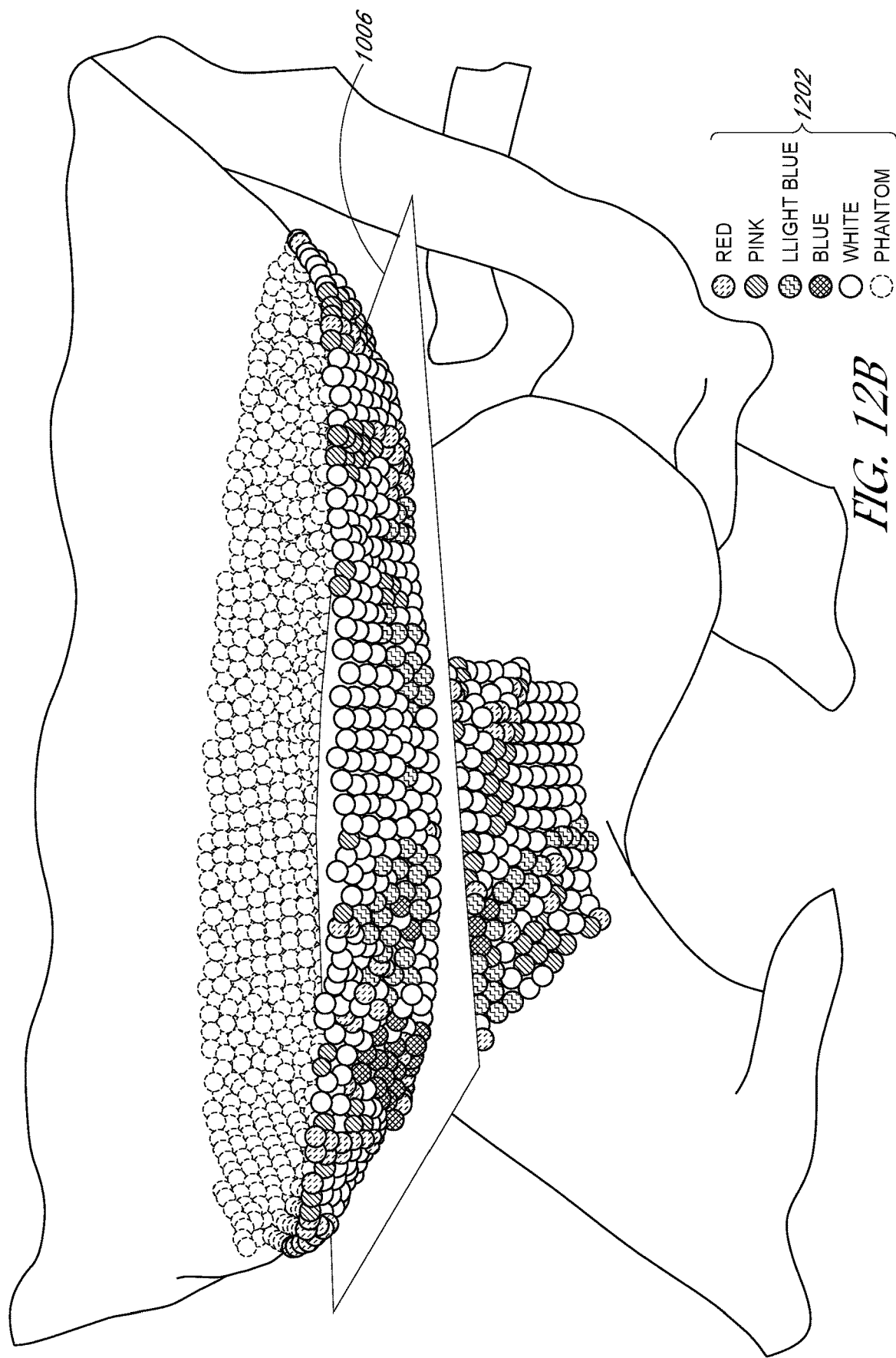

```
                ┌─ 2102
PROVIDING A FIRST IMAGE SEGMENTATION OF A SURFACE OF A BLOOD VESSEL NETWORK
                         │
                         ▼                                    ┌─ 2104
FORMING A FIRST SKELETONIZED GRAPH FROM THE FIRST IMAGE SEGMENTATION,
THE FIRST SKELETONIZED GRAPH COMPRISING A PLURALITY OF EDGE-LINES
                         │
                         ▼                                    ┌─ 2106
IDENTIFYING ONE OR MORE FIRST NODES WITHIN THE FIRST SKELETONIZED
GRAPH, EACH OF THE ONE OR MORE FIRST NODES INTERSECTING MORE THAN
TWO EDGE-LINES OF THE PLURALITY OF EDGE-LINES
                         │
                         ▼                                    ┌─ 2108
IDENTIFYING ONE OR MORE FIRST TERMINAL POINTS WITHIN THE FIRST
SKELETONIZED GRAPH, EACH OF THE ONE OR MORE FIRST TERMINAL POINTS
INTERSECTING ONLY ONE EDGE-LINE OF THE PLURALITY OF EDGE LINES
                         │
                         ▼
PROVIDING A SECOND IMAGE SEGMENTATION       ┌─ 2110
OF A SURFACE OF THE BLOOD VESSEL NETWORK
                         │
                         ▼
FORMING A SECOND SKELETONIZED GRAPH FROM THE SECOND IMAGE
SEGMENTATION, THE SECOND SKELETONIZED GRAPH COMPRISING       ┌─ 2112
A PLURALITY OF EDGE-LINES
                         │
                         ▼                                    ┌─ 2114
IDENTIFYING ONE OR MORE SECOND NODES WITHIN THE SECOND SKELETONIZED
GRAPH, EACH OF THE ONE OR MORE SECOND NODES INTERSECTING MORE
THAN TWO EDGE-LINES OF THE PLURALITY OF EDGE LINES
                         │
                         ▼                                    ┌─ 2116
IDENTIFYING ONE OR MORE SECOND TERMINAL POINTS WITHIN THE SECOND
SKELETONIZED GRAPH, EACH OF THE ONE OR MORE SECOND TERMINAL POINTS
INTERSECTING ONLY ONE EDGE-LINE OF THE PLURALITY OF EDGE LINES
                         │
                         ▼                                    ┌─ 2118
OVERLAPPING THE FIRST SKELETONIZED GRAPH AND THE SECOND SKELETONIZED
GRAPH BY ORIENTING THE ONE OR MORE FIRST NODES WITH THE ONE OR MORE
SECOND NODES AND ORIENTING THE ONE OR MORE FIRST TERMINAL POINTS
WITH THE ONE OR MORE SECOND TERMINAL POINTS
                         │
                         ▼                                    ┌─ 2120
COMPARING GEOMETRY OF THE CEREBRAL ANEURYSM WHEN THE FIRST
SKELETONIZED GRAPH IS OVERLAPPED WITH THE SECOND
SKELETONIZED GRAPH
```

*FIG. 21*

SYSTEMS AND METHODS FOR ANALYTICAL DETECTION OF ANEURYSMS

FIELD OF THE DISCLOSURE

The present invention is generally related to systems and methods for the detection and analysis of aneurysms occurring in blood vessels of the human body including systems and methods for analytical detection of aneurysms. The present invention more particularly relates to systems and methods for detecting aneurysms in the body and then determining the risk of the detected aneurysm to the patient.

BACKGROUND

Aneurysm may occur in blood vessel walls of, for example, the aorta, the abdomen, the brain, capillaries, the heart, the kidneys, and the legs. If undiagnosed or left untreated, the blood-filled aneurysm may rupture the wall of the blood vessel into the surrounding tissue possibly leading to death.

An abdominal aortic aneurysm ("AAA") involves a regional dilation of the aorta. Current technology for detection includes ultrasonography, computed tomography, and magnetic resonance imaging. These technologies are employed to size segments of the aorta and compare those segment to a healthy individual. AAAs are classified by both size and shape. An AAA is usually defined as an outer aortic diameter over 3 cm or more than 50% of normal diameter. The suprarenal aorta normally measures about 0.5 cm larger than the infrarenal aorta. If the outer diameter of the AAA exceeds 5.5 cm, the aneurysm is considered to be large. The presence of abdominal pain, shock, and a pulsatile abdominal mass may indicate the AAA is ruptured. As high as 90 percent of patients die before treatment can be administered for the rupture.

A cerebral aneurysm is a cerebral vascular disorder in which weakness of the wall of a cerebral artery or vein causes a localized dilation or ballooning of the blood vessel wall. Cerebral aneurysms are classified by both size and shape. Smaller aneurysms produce few, if any, symptoms. Larger aneurysms may cause severe headaches, nausea, vision impairment, vomiting and/or loss of consciousness. Larger aneurysms have greater tendency to rupture, but, the majority of ruptured aneurysms are small. About 44 percent of patients die within 1 month after rupture. In addition, ruptured cerebral aneurysms account for about 10 percent of all strokes.

Surgical treatment may be employed for those that survive the rupture of an AAA or cerebral aneurysm. Often the surgical procedure must be employed as soon as possible after rupture for optimal results.

Endovascular treatment involves the insertion of a medical device, such as a coil, inside the aneurysm balloon or inside the affected blood vessel to prevent rebleeding. This procedure is performed intraluminally. Oftentimes, a stent, which is basically an expandable hollow bridge, is used to assist in deploying the coil into the aneurysm sac. The treatment works by promoting blood clotting around the coils, eventually sealing the aneurysm and reducing pressure on its outer wall.

In addition to coils, other endovascular treatments include use of flow diverter stents. Flow diverter stent devices block the opening at the base of the aneurysm (where it meets the vessel wall), preventing blood from flowing into the aneurysm sac. Unfortunately, endovascular treatments carry greater risks when employed post rupture.

If diagnosed prior to rupture, the endovascular treatment may be performed on the patient and mitigate against rupture occurrence. The challenge lies in correctly diagnosing the aneurysm prior to rupture. Technology in medical imaging for early diagnosis of aneurysms often relies on simple comparisons between measured segments of the patient with those of a healthy individual. In certain cases, detection of a cerebral aneurysm begins by reviewing images from 3D rotational-angiography (3DRA), computed tomography angiography (CTA), and/or magnetic resonance angiography (MRA). The detection process then involves a laborious process by a medical provider to visually analyze the images from different geometric points of view with multiple adjustments of contrast/brightness filters. As part of the detection process, the medical provider often manually determines a volume of the aneurysm for further assessment. As such, there is a need to improve diagnostic methods for identifying aneurysms.

SUMMARY

The devices of the present invention have several features, no single one of which is solely responsible for its desirable attributes. Without limiting the scope of this invention as expressed by the claims which follow, its more prominent features will now be discussed briefly. After considering this discussion, and particularly after reading the section entitled "Detailed Description," one will understand how the features of this invention provide several advantages over current designs.

An aspect of the present disclosure provides a method for detecting an aneurysm. The method comprises providing an image segmentation of a surface of a blood vessel network. The image segmentation comprises a plurality of blood vessel surface points. The method includes forming a virtual skeleton model from the image segmentation. The virtual skeleton model comprises a plurality of edges with each edge of the plurality of edges having a plurality of skeleton points. Each skeleton point of the plurality of skeleton points is associated with a subset of the plurality of blood vessel surface points. The method includes identifying inlets and outlets of the virtual skeleton model, virtually fitting elliptically shaped tubules for each edge of the skeletonized graph. determine statistics of the fitted elliptically shaped tubules for each edge, identifying a plurality of potential aneurysms based on the determined statistics, filtering the plurality of potential aneurysms based on the determined statistics, and identifying the aneurysm based at least in part on the filtering.

Another aspect is wherein forming the virtual skeleton model comprises simultaneously determining a medial axis transform of the image segmentation and a mean curvature flow of the image segmentation.

Another aspect is wherein forming the virtual skeleton model comprises determining a medial axis transform of the image segmentation.

Another aspect is wherein forming the virtual skeleton model comprises determining a mean curvature flow of the image segmentation.

Another aspect is wherein identifying the inlets of the virtual skeleton model is based at least in part on determining a distance from each inlet to a flat region formed by one or more of the plurality of blood vessel surface points.

Another aspect is wherein identifying the inlets of the virtual skeleton model is based at least in part on an average distance from each edge to the subset of the plurality of blood vessel surface points associated with the edge.

Another aspect is wherein identifying the outlets of the virtual skeleton model is based at least in part on a skeleton aspect ratio for each edge.

Another aspect is wherein virtually fitting elliptically shaped tubules for each edge of the virtual skeleton model is performed at each skeleton point of the plurality of skeleton points associated with the edge.

Another aspect is wherein determining statistics of the fitted elliptically shaped tubules for each edge comprises one or more of a mean, minimum, maximum, and standard deviations.

Another aspect is wherein determining statistics of the fitted elliptically shaped tubules comprises area statistics for each edge.

Another aspect is wherein filtering the plurality of potential aneurysms based on the determined statistics comprises determining deviations of areas between adjacent ellipses of the elliptically shaped tubules.

Another aspect is wherein determining statistics of the fitted elliptically shaped tubules comprises eccentricity statistics for each edge.

Another aspect is wherein filtering the plurality of potential aneurysms based on the determined statistics comprises determining deviations of eccentricities between adjacent ellipses of the elliptically shaped tubules.

Another aspect is wherein determining statistics of the fitted elliptically shaped tubules comprises volume statistics for each edge, and further comprising filtering the plurality of potential aneurysms to identify false positive (FP) aneurysm cases based on the volume statistics.

Another aspect of the present disclosure provides a system for aneurysm detection and analysis. The system comprises one or more processors configured to provide an image segmentation of a surface of a blood vessel network. The image segmentation comprises a plurality of blood vessel surface points. The one or more processors are further configured to form a virtual skeleton model from the image segmentation. The virtual skeleton model comprises a plurality of edges. Each edge of the plurality of edge lines has a plurality of skeleton points. Each skeleton point of the plurality of skeleton points is associated with a subset of the plurality of blood vessel surface points. The one or more processors are further configured to virtually fit elliptically shaped tubules for each edge of the virtual skeleton model and identify the aneurysm based at least in part on the virtually fit elliptically shaped tubules.

Another aspect is wherein the one or more processors is further configured to determine statistics of the fitted elliptically shaped tubules for each edge.

Another aspect is wherein the one or more processors is further configured to identify a plurality of potential aneurysms based on the determined statistics.

Another aspect is wherein the one or more processors is further configured to filter the plurality of potential aneurysms based on the determined statistics.

Another aspect is wherein the one or more processors is further configured to identify the aneurysm based at least in part on the filtering.

Another aspect is wherein the one or more processors is further configured to identify inlets and outlets of the skeletonized graph.

Another aspect of the present disclosure provides a method for detecting an aneurysm. The method comprises forming a virtual skeleton model comprising a plurality of edges. Each edge of the plurality of edges has a plurality of skeleton points. Each skeleton point of the plurality of skeleton points is associated with a subset of the plurality of blood vessel surface points. The method includes virtually fitting elliptically shaped tubules for each edge of the virtual skeleton model and identifying a potential aneurysm based on the fitted elliptically shaped tubules.

An aspect of the present disclosure provides a method for classifying and measuring a cerebral aneurysm of a parent vessel. The method includes identifying a potential aneurysm and determining whether the potential aneurysm is a saccular aneurysm type or a fusiform aneurysm type. If the potential aneurysm is the saccular aneurysm type then determine a neck-plane, a neck width of the neck-plane, a dome height, and a dome width. If the potential aneurysm is the fusiform aneurysm type then determining a distal plane, a proximal plane, a fusiform length, and a fusiform width.

Another aspect includes wherein the neck-plane comprises a best fit plane that encompasses a boundary between the saccular aneurysm and the parent vessel, and wherein the best fit plane comprises a set of points selected at least in part on whether the set of points have a negative Gaussian curvature.

Another aspect includes wherein the dome height is a maximum distance between a center of the neck-plane and a point on the saccular aneurysm.

Another aspect includes wherein the dome width is a maximum aneurysm width measured perpendicular to a line defining the dome height.

Another aspect includes wherein the distal plane comprises a best fit plane that encompasses a boundary between the fusiform aneurysm and the parent vessel.

Another aspect includes wherein the proximal plane comprises a best fit plane that encompasses a boundary between the fusiform aneurysm and the parent vessel.

Another aspect includes wherein the fusiform length is a length measured along a path between the distal plane and the proximal plane.

Another aspect includes wherein the fusiform width is a length measured perpendicular to the path between the distal plane and the proximal plane.

Another aspect of the present disclosure provides a system for classifying and measuring a cerebral aneurysm of a parent vessel. The system includes one or more processors configured to identify a potential aneurysm and determine whether the potential aneurysm is a saccular aneurysm type or a fusiform aneurysm type. If the potential aneurysm is the saccular aneurysm type then determine a neck-plane, a neck width of the neck-plane, a dome height, and a dome width. If the potential aneurysm is the fusiform aneurysm then determine a distal plane, a proximal plane, a fusiform length, and a fusiform width.

Another aspect includes wherein the neck-plane comprises a best fit plane that encompasses a boundary between the saccular aneurysm and the parent vessel, and wherein the best fit plane comprises a set of points selected at least in part on whether the set of points have a negative Gaussian curvature.

Another aspect includes wherein the dome height is a maximum distance between a center of the neck-plane and a point on the saccular aneurysm.

Another aspect includes wherein the dome width is a maximum aneurysm width measured perpendicular to a line defining the dome height.

Another aspect includes wherein the distal plane comprises a best fit plane that encompasses a boundary between the fusiform aneurysm and the parent vessel.

Another aspect includes wherein the proximal plane comprises a best fit plane that encompasses a boundary between the fusiform aneurysm and the parent vessel.

Another aspect includes wherein the fusiform length is a length measured along a path between the distal plane and the proximal plane.

Another aspect includes wherein the fusiform width is a length measured perpendicular to the path between the distal plane and the proximal plane.

Another aspect of the present disclosure provides a method for classifying and measuring a cerebral aneurysm of a parent vessel. The method includes identifying a potential aneurysm and determining whether the potential aneurysm is a saccular aneurysm type or a fusiform aneurysm type. If the potential aneurysm is the saccular aneurysm type then determine a neck-plane and a neck width of the neck-plane. If the potential aneurysm is the fusiform aneurysm type then determine a distal plane and a proximal plane.

Another aspect includes wherein the neck-plane comprises a best fit plane that encompasses a boundary between the saccular aneurysm and the parent vessel, and wherein the best fit plane comprises a set of points selected at least in part on whether the set of points have a negative Gaussian curvature.

Another aspect includes wherein the distal plane comprises a best fit plane that encompasses a boundary between the fusiform aneurysm and the parent vessel.

Another aspect includes wherein the proximal plane comprises a best fit plane that encompasses a boundary between the fusiform aneurysm and the parent vessel.

An aspect of the present disclosure provides a method for identifying growth of a cerebral aneurysm. The method includes providing a first image segmentation of a surface of a blood vessel network. The first image segmentation comprises a first plurality of blood vessel surface points. The method includes forming a first virtual skeleton model from the first image segmentation. The first virtual skeleton model comprises a plurality of edges. Each edge of the plurality of edges has a plurality of skeleton points. Each skeleton point of the plurality of skeleton points is associated with a subset of the plurality of blood vessel surface points. The method includes identifying one or more first nodes within the first virtual skeleton model. Each of the one or more first nodes intersects more than two edges of the plurality of edges. The method includes providing a second image segmentation of a surface of the blood vessel network. The second image segmentation comprises a second plurality of blood vessel surface points. The method includes forming a second virtual skeleton model from the second image segmentation. The second virtual skeleton model comprises a plurality of edges. Each edge of the plurality of edges has a plurality of skeleton points. Each skeleton point of the plurality of skeleton points is associated with a subset of the plurality of blood vessel surface points. The method includes identifying one or more second nodes within the second virtual skeleton model. Each of the one or more second nodes intersects more than two edges of the plurality of edges. The method includes overlapping the first virtual skeleton model and the second virtual skeleton model by orienting the one or more first nodes with the one or more second nodes.

Another aspect is comparing geometry of the cerebral aneurysm when the first virtual skeleton model is overlapped with the second virtual skeleton model.

Further aspects are identifying one or more first terminal points within the first virtual skeleton model, each of the one or more first terminal points intersecting only one edge of the plurality of edges, identifying one or more second terminal points within the second virtual skeleton model, each of the one or more second terminal points intersecting only one edge of the plurality of edges, and overlapping the first virtual skeleton model and the second virtual skeleton model by orienting the one or more first terminal points with the one or more second terminal points.

Another aspect is wherein the one or more first nodes is a bifurcation point.

Another aspect is wherein the one or more first nodes is part of a cycle.

Another aspect of the present disclosure provides a system for identifying growth of a cerebral aneurysm. The system comprises one or more processors configured to provide a first image segmentation of a surface of a blood vessel network. The first image segmentation comprises a first plurality of blood vessel surface points. The one or more processors are further configured to form a first virtual skeleton model from the first image segmentation. The first virtual skeleton model comprises a plurality of edges. Each edge of the plurality of edges has a plurality of skeleton points. Each skeleton point of the plurality of skeleton points is associated with a subset of the plurality of blood vessel surface points. The one or more processors are further configured to identify one or more first nodes within the first virtual skeleton model. Each of the one or more first nodes intersects more than two edges of the plurality of edges. The one or more processors are further configured to provide a second image segmentation of a surface of the blood vessel network. The second image segmentation comprises a second plurality of blood vessel surface points. The one or more processors are further configured to form a second virtual skeleton model from the second image segmentation. The second virtual skeleton model comprises a plurality of edges. Each edge of the plurality of edges has a plurality of skeleton points. Each skeleton point of the plurality of skeleton points is associated with a subset of the plurality of blood vessel surface points. The one or more processors are further configured to identify one or more second nodes within the second virtual skeleton model. Each of the one or more second nodes intersects more than two edges of the plurality of edges. The one or more processors are further configured to overlap the first virtual skeleton model and the second virtual skeleton model by orienting the one or more first nodes with the one or more second nodes.

Another aspect is wherein the one or more processors are further configured to compare geometry of the cerebral aneurysm when the first virtual skeleton model is overlapped with the second virtual skeleton model.

Further aspects are wherein the one or more processors are further configured to identify one or more first terminal points within the first virtual skeleton model, each of the one or more first terminal points intersecting only one edge of the plurality of edges, identify one or more second terminal points within the second virtual skeleton model, each of the one or more second terminal points intersecting only one edge of the plurality of edges, and overlap the first virtual skeleton model and the second virtual skeleton model by orienting the one or more first terminal points with the one or more second terminal points.

Another aspect is wherein the one or more first nodes is a bifurcation point.

Another aspect is wherein the one or more first nodes is part of a cycle.

Another aspect is wherein the one or more second nodes is a bifurcation point.

Another aspect is wherein the one or more second nodes is part of a cycle.

Another aspect of the present disclosure provides a method for identifying growth of a cerebral aneurysm. The method comprises providing a first image segmentation of a surface of a blood vessel network. The first image segmentation comprises a first plurality of blood vessel surface points. The method includes forming a first virtual skeleton model from the first image segmentation. The first virtual skeleton model comprises a plurality of edges. Each edge of the plurality of edges has a plurality of skeleton points. Each skeleton point of the plurality of skeleton points is associated with a subset of the plurality of blood vessel surface points. The method includes identifying one or more first terminal points within the first virtual skeleton model. Each of the one or more first terminal points intersects only one edge of the plurality of edges. The method includes providing a second image segmentation of a surface of the blood vessel network. The second image segmentation comprises a second plurality of blood vessel surface points. The method includes forming a second virtual skeleton model from the second image segmentation. The second virtual skeleton model comprises a plurality of edges. Each edge of the plurality of edges has a plurality of skeleton points. Each skeleton point of the plurality of skeleton points is associated with a subset of the plurality of blood vessel surface points. The method includes identifying one or more second terminal points within the second virtual skeleton model. Each of the one or more second terminal points intersects only one edge of the plurality of edges. The method includes overlapping the first virtual skeleton model and the second virtual skeleton model by orienting the one or more first terminal points with the one or more second terminal points.

Another aspect is comparing geometry of the cerebral aneurysm when the first virtual skeleton model is overlapped with the second virtual skeleton model.

Further aspects are identifying one or more first nodes within the first virtual skeleton model, each of the one or more first nodes intersecting more than one edge of the plurality of edges, identifying one or more second nodes within the second virtual skeleton model, each of the one or more second nodes intersecting more than one edge of the plurality of edges, and overlapping the first virtual skeleton model and the second virtual skeleton model by orienting the one or more first nodes with the one or more second nodes.

Another aspect is wherein the one or more first nodes is a bifurcation point.

Another aspect is wherein the one or more first nodes is part of a cycle.

Another aspect is wherein the one or more second nodes is a bifurcation point.

Another aspect is wherein the one or more second nodes is part of a cycle.

Another aspect is wherein the one or more first nodes is a vertex.

Further aspects features and advantages of the present invention will become apparent from the detailed description that follows.

BRIEF DESCRIPTION OF THE DRAWINGS

These and other features, aspects, and advantages of the present invention will now be described in connection with embodiments of the present invention, in reference to the accompanying drawings. The illustrated embodiments, however, are merely examples and are not intended to limit the invention. Some embodiments will be described in conjunction with the appended drawings, where like designations denote like elements.

Embodiments of the invention will now be described, by way of example only, with reference to the accompanying drawings in which corresponding reference symbols indicate corresponding parts.

FIGS. 12A and 12B illustrate exemplary measurements and dimensions of a saccular aneurysm.

FIG. 21 illustrates a method for comparing geometry of a cerebral aneurysm over a period of time.

Figure 1:
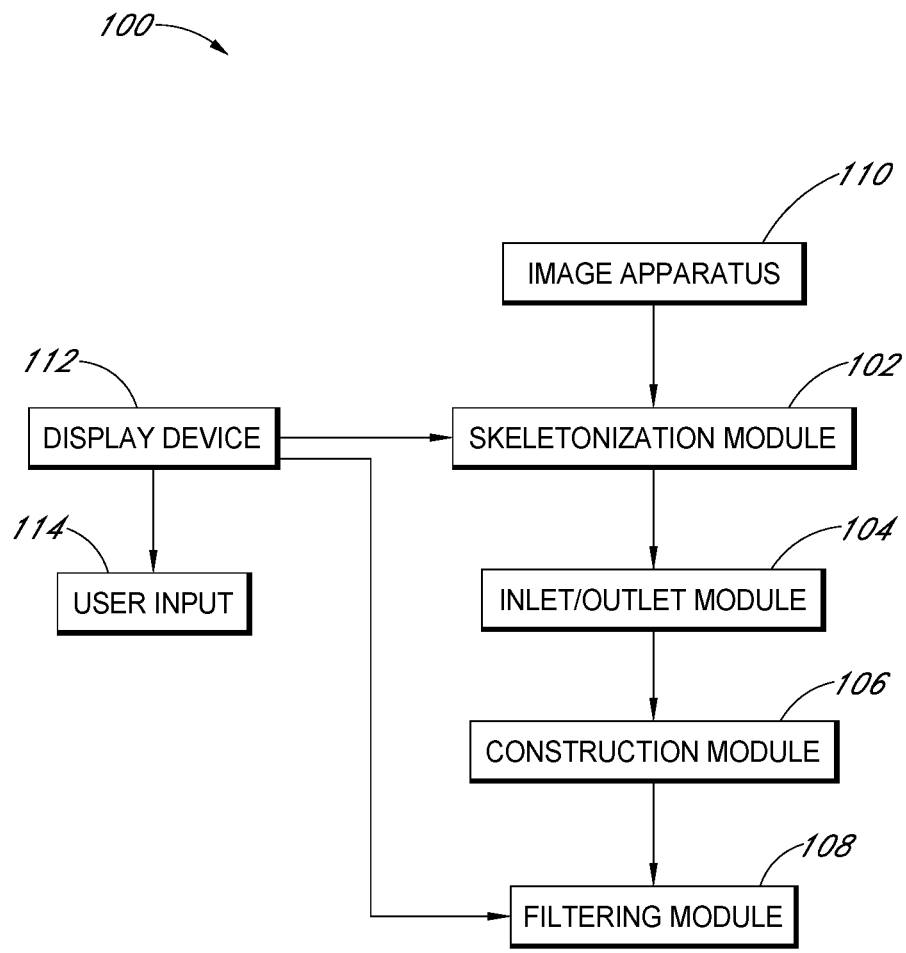
FIG. 1 depicts a computer system for aneurysm detection and analysis in accordance with an exemplary embodiment of the present invention.

The various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Definitions

As used in this description and the accompanying claims, the following terms shall have the meanings indicated, unless the context otherwise requires:

Graph is a mathematical structure used to model pairwise relations between objects (like nodes, points, vertices etc.). Pairwise relations between relations itself are called edges (also called links or lines).

Bifurcation in context of graph is a node that has more than two edges attached.

Terminal point denotes a node (or point) that has only one edge/line attached.

Path is a collection of edges/lines (can be just one edge) connecting two nodes or points.

Cycle in graph is a path of edges and nodes wherein a vertex is reachable from itself.

Inlet/outlet points are terminal points of blood vessel network, represented as graph, and denote blood flow inlets/outlets.

Segmentation is a surface representation of blood vessel network obtained from raw pixel image.

Overview

FIG. 1 depicts a computer system 100 for aneurysm detection and analysis in accordance with an exemplary embodiment of the present invention. In certain embodiments, the computer system 100 comprises one or more of a skeletonization module 102, an inlet/outlet module 104, a construction module 106, and a filtering module 108. In certain embodiments, the computer system 100 comprises one or more of an image apparatus 110, a display device 112, and a user input 114.

As will be explained in more detail with respect to FIGS. 4A and 4B, the skeletonization module 102 is configured to create a virtual skeleton model of a blood vessel network. In certain embodiments, the virtual skeleton model is represented by a graph. In certain embodiments, the graph is a mathematical structure used to model pairwise relations between objects. Objects can include, for example, nodes, points, and vertices within the virtual skeleton model. Pairwise relations between relations itself are called edges. Edges can include links or lines within the virtual skeleton model.

In certain embodiments, the virtual skeleton model of the blood vessel network is at least created in part based on images taken of the blood vessel network. In certain embodiments, the virtual skeleton model represents the entire blood vessel network. In certain embodiments, the virtual skeleton model captures the topology and major geometry of the whole blood vessel network including any aneurysm present in the blood vessel network. In certain embodiments, the virtual skeleton model represents not only healthy vessels but also unhealthy vessels such as an aneurysm to create a complete virtual picture of the blood vessel network. In certain embodiments, the virtual skeleton model represents a plurality of skeleton points. Each skeleton point is defined by a plurality of blood vessel surface points. The plurality of blood vessel surface points corresponds to points on the images of the blood vessel network.

In certain embodiments, the skeletonization module 102 employs an algorithm to create the virtual skeleton model. In certain embodiments, the skeletonization module 102 employs a mean curvature skeleton method for creating the virtual skeleton model. In certain embodiments, the mean curvature skeleton method comprises a single method or a combination of more than one method. In embodiments comprising more than one method, the methods may be employed in series or in parallel. For example, the first method and the second method may be employed simultaneously to create the virtual skeleton model.

In certain embodiments, the virtual skeleton model is created by the mean curvature skeleton method grasping the topology of the blood vessel network as well as essential geometric features of the blood vessel network such as big bulges, but ignores small geometric features of the blood vessel network including "noisy" artifacts. The resulting virtual skeleton model is a skeleton of the blood vessel network and is in a form of a tree graph structure. In certain embodiments, tree graph edges that connect nodes represent center lines of the blood vessel surface. In certain embodiments, points that belong to a single edge represent terminal points. In certain embodiments, points that belong to more than two edges are represented as a bifurcation. In certain embodiments, the tree graph is broken into edges based on the bifurcations.

As will be explained in more detail with respect to FIGS. 5A and 5B, the inlet/outlet module 104 is configured to identify inlets and outlets of the vasculature within the virtual skeleton model created by the skeletonization module 102. The inlets and outlets denote blood flow direction into and out of the virtual skeleton model of the vasculature. In certain embodiments, the identification of the inlets and outlets is performed automatically. In certain embodiments, the identification of the inlets and outlets is performed semi-automatically. In certain embodiments, the identification of the inlet is performed semi-automatically while the identification of the outlet is performed automatically. In certain embodiments, the identification of the outlet is performed semi-automatically while the identification of the inlet is performed automatically.

In certain embodiments, the inlet/outlet module 104 identifies the inlets and outlets based on geometry of the virtual skeleton model. For example, in certain embodiments, the inlet/outlet module 104 identifies inlets and outlets based at least in part on characteristics of the plurality of skeleton points determined by the skeletonization module 102.

Exemplary methods for identifying an inlet include a plane method and a default method. However, the method for identifying the inlet is not limited to the recited methods and includes changes and modifications to the disclosed methods that would be known by a person having ordinary skill in the art. The method can include identifying a cutting plane based on specific geometry of the surface mesh. In certain embodiments, the identified specific geometry are large, flat regions on the surface mesh. Once the cutting plane is identified, the inlets are identified as terminal points within a certain distance of the identified cutting plane.

As will be explained in more detail with respect to FIGS. 6A and 6B, the construction module 106 is configured to fit one or more predefined geometric shapes to the virtual skeleton model created by the skeletonization module 102. In certain embodiments, the construction module 106 is configured to fit the one or more predefined geometric shapes to each edge created by the skeletonization module 102. In certain embodiments, at least one of the predefined geometric shapes is an ellipse. Adjacent fitted ellipses may form elliptically shaped tubules. Of course the method is not limited to constructing and fitting ellipses and may include other shapes as well as combinations of different shapes.

In certain embodiments, the construction module 106 fits the ellipses in a plane that is orthogonal to a tangent vector of the edge. In certain embodiments, the tangent vector is smoothed before defining the orthogonal plane. In certain embodiments, the smoothing is a one-step averaging smoothing.

In certain embodiments, the construction model 106 determines statistics related to the one or more predefined geometric shapes fitted to the virtual skeleton model. In certain embodiments, the statistics are used by, for example, the filtering module 108. These statistics can include mean, minimum, maximum, and standard deviations for the parameters of each of the one or more predefined geometric shape fitted along each edge. Of course, these statistics are not limited to the listed statistics and can include other statistics that would be known by a person having ordinary skill in the art.

As will be explained in more detail with respect to FIGS. 7A and 7B, the filtering module 108 is configured to identify potential aneurysms within the virtual skeleton model of the blood vessel network. In certain embodiments, the filtering module 108 analyzes the one or more predefined geometric shapes fitted by the construction module 106 to the virtual skeleton model along with one or more of the statistics generated for the parameters of the one or more predefined geometric shapes determined by the construction model 106.

In certain embodiments, the filtering module 108 perform one or more filtering steps to the virtual skeleton model so as to identify potential aneurysms within the virtual skeleton model. In certain embodiments, the one or more filtering steps are based on one or more of the statistics determined by the construction model 106. In certain embodiments, the filtering module 108 filters the virtual skeleton model based on one or more statistics for the parameters of each of the one or more predefined geometric shapes fitted along each edge. In certain embodiments, the one or more statistics include the mean, minimum, maximum, and standard deviations of the parameters for each of the one or more predefined geometric shapes. In certain embodiments, one or more of the steps within the one or more filtering steps are repeated or iterated to further identify additional potential aneurysms in the virtual skeleton model.

In certain embodiments, the one or more filtering steps include a step based on ellipse area statistics. For example, filtering based on ellipse area statistics can include statistically filtering each edge based on the ellipse area. In certain embodiments, the one or more filtering steps include a step based on ellipse eccentricity statistics. The variation in the eccentricity may be indicative of a potential aneurysm even though there is little deviation in the area across adjacent ellipses.

In certain embodiments, the filtering module 108 flags skeleton points within the virtual skeleton model as potential aneurysm and then removes the flagged skeleton points from the virtual module based on a comparison of the eccentricity calculated for the ellipse and an eccentricity threshold value.

In certain embodiments, the filtering module 108 determines one or more volumes. The filtering module 108 determined one or more volumes related to the potential aneurysms. In certain embodiments, the filtering module 108 compares the volume of a healthy vessel in the region of the potential aneurysms with the volume of the potential aneurysms.

The comparison between the volumes indicates whether the potential aneurysms is a true positive or is a false positive. In certain embodiments, if the volume of the potential aneurysm is not greater than some tolerance plus the virtual volume of the healthy vessel in the region of the potential aneurysms then the potential aneurysms is a false positive.

Aneurysm Measurement

As will be further explained below, in certain embodiments after the detection steps are performed, identified potential aneurysms are shown in the display device 112 for final selection by the healthcare provider. The healthcare provider screens out false positives from the list of potential aneurysms using the user input 114. In certain embodiments, there are no more than a few false positives per case and those false positives are easily screened out by the healthcare provider via the display device 112. In certain embodiments, the user input 114 allows the healthcare provider to adjust the type of aneurysm (fusiform or saccular) for the aneurysms selected.

Aneurysm Comparison

As will be further explained below, given multiple scans of the same patient taken over a period of time, the healthcare provider can track and monitor the aneurysm growth. Certain features of the skeleton graph (for example, bifurcations and graph structure) created by the skeletonization module 102 will remain relatively constant, even if the positions, orientations, or extent of vasculature differ between the segmentations. In certain embodiments, these features are used to orient the two geometries with respect to one another. After the geometries are oriented, the identified aneurysms from each geometry are matched and measurements are compared.

Some embodiments of the system 100, which is used for analysis and/or display of vascular information for a patient, include some or all of the components shown in FIG. 1. The image apparatus 110 is used to determine, analyze, and/or display vascular information for a patient. In certain embodiments, the image apparatus 110 is a Computed Tomography (CT) or Magnetic Resonance (MR) apparatus. In certain embodiments, the image apparatus 110 produces 3D image data or scans for the patient. In some examples, this data is in the form of a series of cross-sectional data scans. This data is represented, for instance through a process of resampling or other form of image processing. In certain embodiments, the image apparatus 110 provides the 3D image data or scans to the skeletonization module 102 for further processing.

In the system shown in FIG. 1, the display device 112 is used to produce a presentation image for presentation to a healthcare provider. For instance, the presentation image shows the results of one or more of the skeletonization module 102, the inlet/outlet module 104, the construction module 106, and the filtering module 108. In certain embodiments, the presentation image is a view of a three-dimensional image. In certain embodiments, an originally acquired image is enhanced to indicate locations of potential aneurysms and/or regions of the vasculature that have a high degree of abnormality.

In the system shown in FIG. 1, the user input 114 allows the healthcare provider to review, analyze, modify, and select at least a portion of the results from one or more of the skeletonization module 102, the inlet/outlet module 104, the construction module 106, and the filtering module 108. In certain embodiments, the healthcare provider confirms/re-selects inlet ports identified by the inlet/outlet module 104 and/or screens false positives identified by the filtering module 108 via the user input 114.

Figure 2:
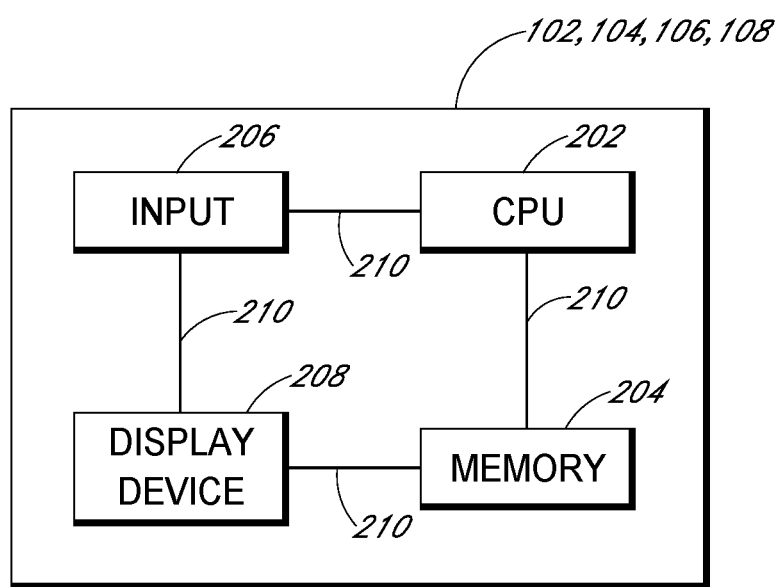
FIG. 2 is an exemplary representation of any of the modules of the computer system including the skeletonization module, the inlet/outlet module, the construction module, and the filtering module from FIG. 1.

FIG. 2 is an exemplary representation of any of the modules of the computer system 100 including the skeletonization module 102, the inlet/outlet module 104, the construction module 106, and the filtering module 108 from FIG. 1.

The skeletonization module 102, the inlet/outlet module 104, the construction module 106, and/or the filtering module 108 can each comprise, inter alia, a central processing unit (CPU) 202, a memory 204, and a display 208. A bus input/output (I/O) interface 210 couples the skeletonization module 102, the inlet/outlet module 104, the construction module 106, and/or the filtering module 108. In certain embodiments, each of the skeletonization module 102, the inlet/outlet module 104, the construction module 106, and/or the filtering module 108 are generally coupled to various input devices 206 such as a mouse and keyboard through the bus I/O interface 210 to the display 208. In certain embodiments, one or more of the skeletonization module 102, the inlet/outlet module 104, the construction module 106, and/or the filtering module 108 share a common input device 206 and/or display 208. In certain embodiments, the input device 206 is the same as the user input 114 described with respect to FIG. 1. In certain embodiments, the display 208 is the same as the display device 112 described with respect to FIG. 1.

The bus I/O interface 210 can include circuits such as cache, power supplies, clock circuits, and a communications bus. The memory 204 can include RAM, ROM, disk drive, tape drive, etc., or a combination thereof. Exemplary disclosed embodiments may be implemented as a subroutine, routine, program, software, stored in the memory 204 (e.g., a non-transitory computer-readable storage medium) and executed by the CPU 202 to process data. As such, any of the skeletonization module 102, the inlet/outlet module 104, the construction module 106, and/or the filtering module 108 can be implemented as a general-purpose computer system that becomes a specific purpose computer system when executing the subroutine, routine, program, software, stored in the memory 204.

In certain embodiments, any of the skeletonization module 102, the inlet/outlet module 104, the construction module 106, and/or the filtering module 108 can also include an operating system and micro-instruction code. The various processes and functions described herein may either be part of the micro-instruction code or part of the application program (or a combination thereof) which is executed via the operating system. In addition, various other peripheral devices may be connected to the computer system 100 such as an additional data storage device and a printing device.

Figure 3:
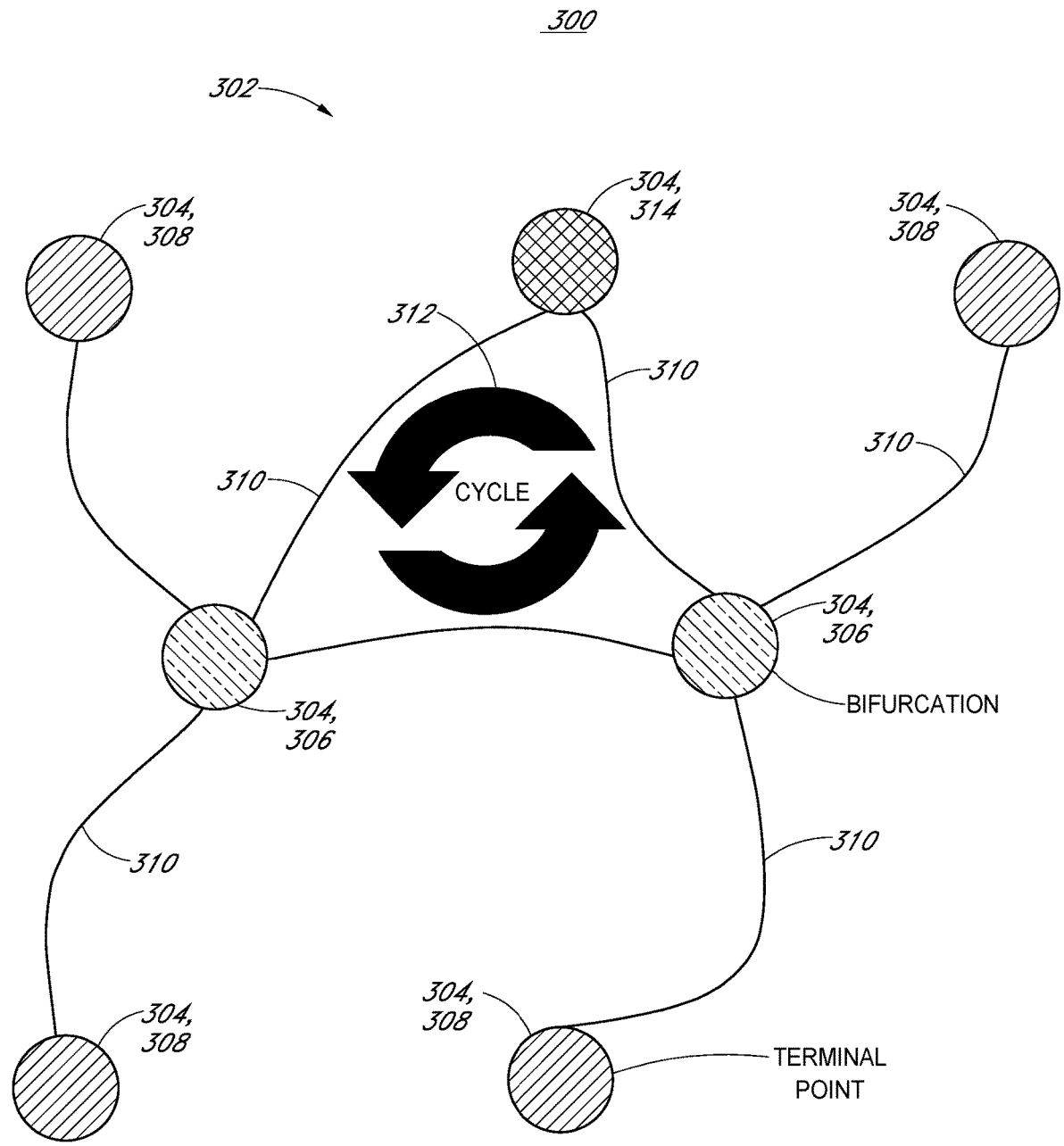
FIG. 3 is a representation of an exemplary graph of a blood vessel network showing certain objects of the blood vessel network.

FIG. 3 is a representation of an exemplary graph 300 of a blood vessel network 302 showing certain objects of the blood vessel network 302. The blood vessel network 302 in FIG. 3 is simplified in that the blood vessel network 302 is represented by points and lines. A visual representation of surfaces of the blood vessel network 302 is not provided in FIG. 3. However, as will be explained with respect to FIG. 4, the graph 300 is derived from geometric features such as, for example, surfaces and shapes representing the blood vessel network 302 of the patient. In certain embodiments, the graph 300 is a mathematical structure used to model pairwise relations between objects of the blood vessel network 302. Exemplary objects include nodes or points 304 and vertices 314. Other objects are within the scope of this disclosure.

In certain embodiments, the node or point 304 is classified as a bifurcation point 306 or a terminal point 308. The classification can depend on, for example, the node or point 304 connection(s) and position within the blood vessel network 302. In certain embodiments, pairwise relations between relations itself are called links, lines, or edges 310. For ease of explanation, a node or point 304 classified as a bifurcation point 306 in the context of the graph 300 is a node or point 304 that is attached to more than two edges 310. For example, FIG. 3 illustrates two bifurcation points 306.

In certain embodiments, the node or point 304 classified as a terminal point 308 in the context of the graph 300 is a node or point 304 that is attached to only one edge 310. For example, FIG. 3 illustrates four terminal points 308.

In certain embodiments, a path is defined as at least one edge 310 connecting two nodes or points 304. Thus, each edge 310 is a path. If the path includes a plurality of edges 310 and a plurality of nodes or points 304 from which the path can connect a vertex 314 to itself, the path is then classified as a cycle 312. An exemplary cycle 312 is illustrated in FIG. 3.

Figure 4A:
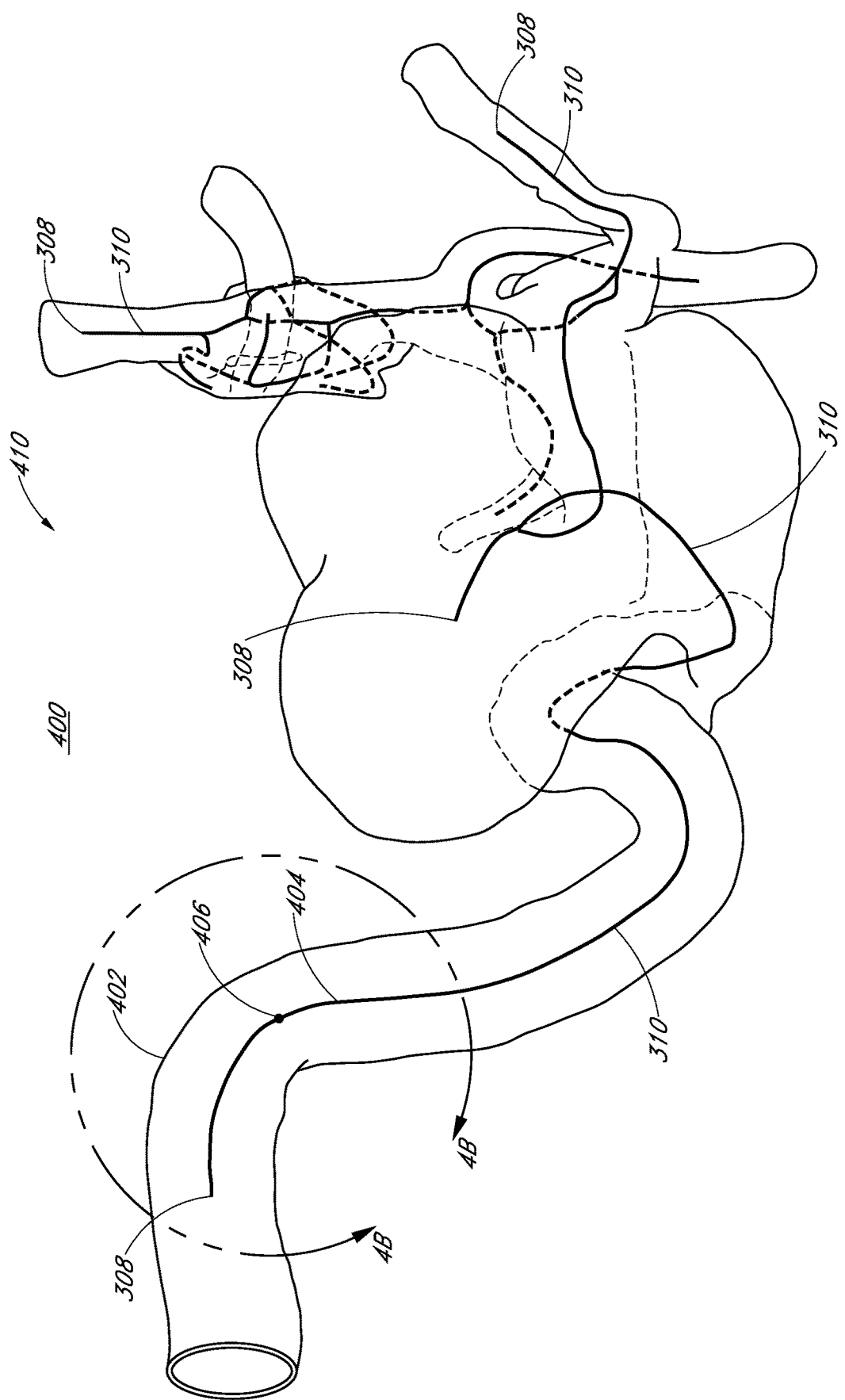
FIG. 4A illustrates a virtual skeleton model of a blood vessel network.

FIG. 4A illustrates a virtual skeleton model 400. The virtual skeleton model 400 is created by the skeletonization module 102 from an exemplary blood vessel network 402 of a patient. In certain embodiments, the skeletonization module 102 is configured to create the virtual skeleton model 400 of the blood vessel network 402. The blood vessel network 402 of the patient is shown for convenience to understand the process performed by the skeletonization module 102 to create the virtual skeleton model 400 of the blood vessel network 402. Once created and in certain embodiments, the virtual skeleton module 400 represents some or all of the geometric features of the blood vessel network 402. In certain embodiments, the virtual skeleton module 400 represents a subset of the geometric features of the blood vessel network 402.

In certain embodiments, the virtual skeleton model 400 is represented by a graph 404. An exemplary graph 300 is illustrated in FIG. 3. In certain embodiments, the graph 404 is a mathematical structure used to model pairwise relations between objects that represent geometric features of the blood vessel network 402. Objects can include, for example as is illustrated in FIG. 3, nodes/points 304 and vertices 314 within the virtual skeleton model 400.

In certain embodiments, the nodes or points 304 are classified as a bifurcation point 306 or a terminal point 308. In FIG. 4A, multiple nodes or points 304 and identified as terminal points 308. As explained with respect to FIG. 3, pairwise relations between relations such as nodes or points 304 are called edges 310. Edges 310 can include links or lines within the virtual skeleton model 400.

In certain embodiments, the virtual skeleton model 400 represents at least a portion of the blood vessel network 402. In certain embodiments, the blood vessel network 402 is created in part based on images taken of the blood vessel network 402. In certain embodiments, the image apparatus 110 from FIG. 1 provides the images used to create a model of the blood vessel network 402. In certain embodiments, the image apparatus 110 provides images from 3D rotational-angiography (3DRA), computed tomography angiography (CTA), and/or magnetic resonance angiography (MRA). In certain embodiments, images provided by the image apparatus 110 provide different geometric points of view of the blood vessel network 402.

From the model of the blood vessel network 402, the skeletonization module 102 creates the virtual skeleton model 400. In certain embodiments, the virtual skeleton model 400 represents the entire blood vessel network 402. For example, the virtual skeleton model 400 can represent the blood vessel network 402 of the entire body of the patient. In certain embodiments, the virtual skeleton model 400 captures the topology and major geometry of the entire blood vessel network 402 including any potential aneurysm present in the entire blood vessel network 402. In certain embodiments, the virtual skeleton model 400 represents a subset of the blood vessel network 402. In certain embodiments, the virtual skeleton model 400 represents the blood vessel network 402 in a targeted region of the body. For example in certain embodiments, the virtual skeleton model 400 represents the blood vessel network 402 in the brain.

In certain embodiments, the virtual skeleton model 400 represents not only healthy blood vessels but also unhealthy blood vessels. In this way, the virtual skeleton model 400 includes unhealthy blood vessels, such as a potential aneurysm, to create a complete virtual skeleton model 400 of the blood vessel network 402.

In certain embodiments, the virtual skeleton model 400 is represented by the graph 404. In certain embodiments, the graph 404 comprises one or more edges 310 as described with respect to FIG. 3. Each edge 310 of the graph 404 can comprise or be associated with one or more skeleton points 406. In this way, a series of adjacent skeleton points 406 defines at least a portion of the edge 310.

In certain embodiments, adjacent skeleton points 406 are separated by a distance. In certain embodiments, the distance between a first skeleton point 406 and an adjacent skeleton point 406 is predetermined. In certain embodiments, the distance between the first skeleton point 406 and the adjacent skeleton point 406 is determined during the skeletonization process. In certain embodiments, the distance between adjacent skeleton points 406 varies along the edge 310 comprising the adjacent skeleton points 406.

In certain embodiments, one or more intermediate skeleton points 406 between the first skeleton point 406 and the second skeleton point 406 is determined. For example in certain embodiments, the one or more intermediate points 406 are determined based on interpolation. In certain embodiments, the interpolation is based on one or more skeleton points 406 of the edge 310.

Figure 4B:
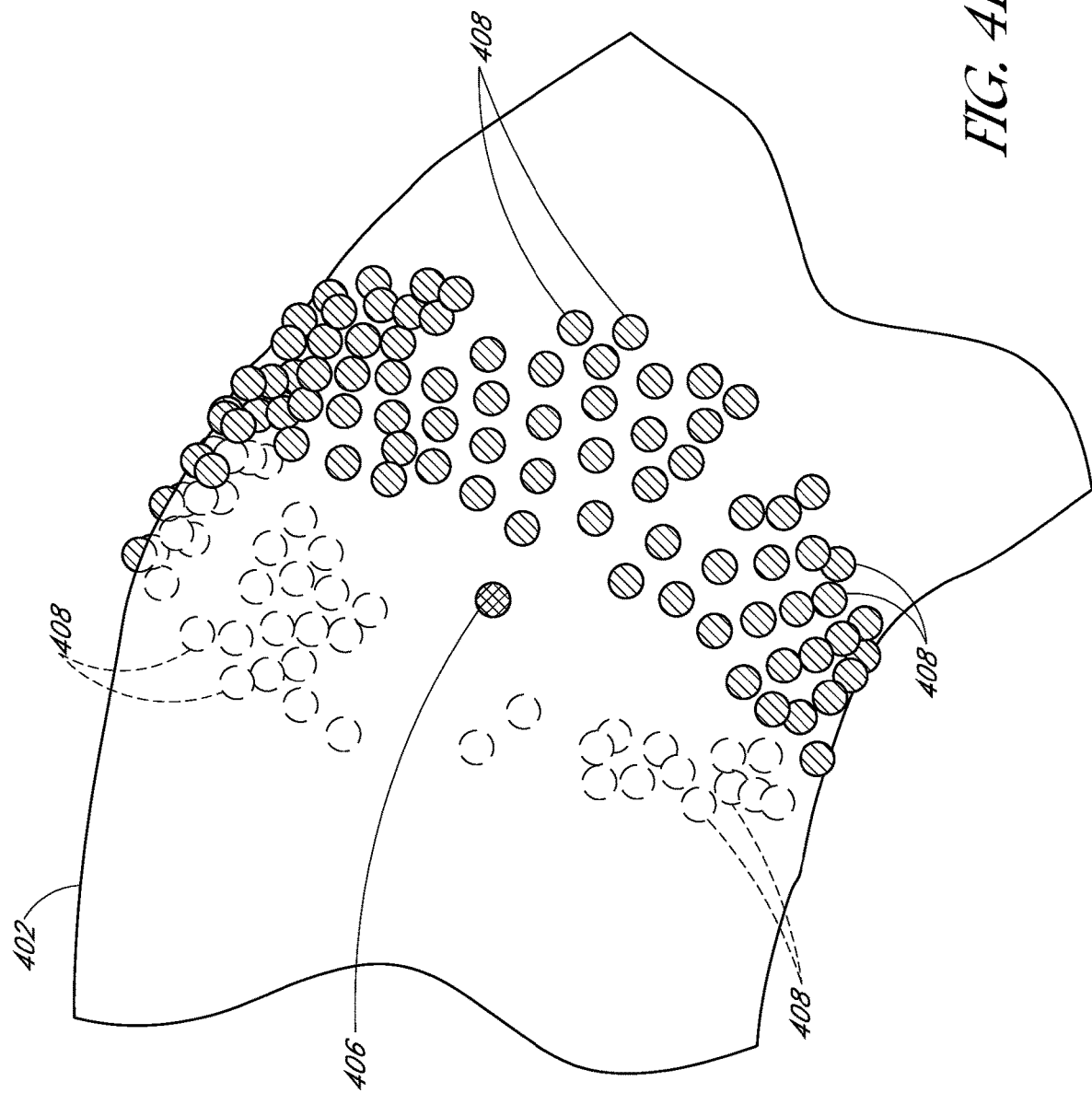
FIG. 4B is a view of a portion of the blood vessel network taken along lines 4B-4B of FIG. 4A and illustrates one or more surface points of the blood vessel network and a single skeleton point associated with the one or more surface points.

FIG. 4B is a view of a portion of the blood vessel network 402 taken along lines 4B-4B of FIG. 4A and illustrates one or more surface points 408 of the blood vessel network 402 and a single skeleton point 406 associated with the one or more surface points 408. As disclosed above, the edge 310 of the graph 404 comprises one or more skeleton points 406. In certain embodiments, each of the skeleton points 406 is associated with or represents one or more surface points 408. In this way, the skeletonization module 102 processes the images provided by the image apparatus 110 to create surfaces of the blood vessel network 402.

The surface of the blood vessel network 402 comprises or is represented by the one or more surface points 408. The one or more surface points 408 correspond to points on one or more images of the blood vessel network 402. Based at least in part on the one or more surface points 408, the skeletonization module 102 determines the one or more skeleton points 406. In this way, a portion of the surface of the entire blood vessel network 402 is efficiently represented by a single skeleton point 406.

The number of surface points 408 represented by a single skeleton point 406 can vary. In certain embodiments, a single skeleton point 406 represents 100 surface points 408. In certain embodiments, a single skeleton point 406 represents 1,000 surface points 408. In certain embodiments, a single skeleton point 406 represents 10,000 surface points 408.

In certain embodiments, each skeleton point 406 represents surface points 408 in proximity to the skeleton point 406. For example, the skeleton point 406 can represent a plurality of surface points 408 in the region of or in close proximity to the skeleton point 406. In FIG. 4B, the skeleton point 406 represents a plurality of surface points 408 defining a circumference of the blood vessel network 402 proximal to the skeleton point 406. Of course, the disclosure is not so limited. In certain embodiments, the plurality of surface points 408 and spaced from their associated skeleton point 406.

In certain embodiments, not all the surface points 408 within a plurality of surface points 408 associated with a single skeleton point 406 need have the same properties or geometric features. In certain embodiments, the surface points 408 associated with the same skeleton point 406 have different properties or geometric features. In certain embodiments, the different properties or geometric features for the surface points 408 associated with the same skeleton point 406 are at least a factor employed by the skeletonization module 102 when determining or defining the skeleton point 406 which will represent the surface points 408.

In certain embodiments, a first weight is associated with a certain property or geometric feature of a first surface point 408 and a second weight is associated with a certain property or geometric feature of a second surface point 408. In certain embodiments, the weights are a factor used by the skeletonization module 102 when determining the skeleton point 406 to associate with the first and second surface points 408.

In certain embodiments, the skeletonization module 102 employs an algorithm to create the virtual skeleton model 400. In certain embodiments, the skeletonization module 102 employs a mean curvature method 410 for creating the virtual skeleton model 400.

In certain embodiments, the mean curvature method 410 comprises a single method or algorithm or a combination of more than one method or algorithm. In embodiments comprising more than one method, the methods may be employed in series in certain embodiments, in parallel in certain embodiments, concurrently or overlapping in duration in certain embodiments, and simultaneously in certain embodiments. For example, the first method and the second method may be employed simultaneously to create the virtual skeleton model 400.

In certain embodiments, the mean curvature method 410 comprises a first method and a second method. In certain embodiments, the first method is a medial axis method. In certain embodiments, the medial axis method is based on a medial axis transform ("MAT"). In certain embodiments, the virtual skeleton model 400 created by the medial axis method provides a virtual skeleton model 400 that includes points at centers of maximally inscribed spheres. In certain embodiments, to create the virtual skeleton model 400, the medial axis method grasps all of the geometry of the surface shape. The grasp shape is a true dual shape representation. By grasping all of the geometry, the virtual skeleton model 400 will include any "noisy" artifacts of the surface shape of the blood vessel network 402 in the virtual skeleton model 400.

In certain embodiments where the mean curvature method 410 comprises a first method and a second method, the second method can be a mean curvature flow method. In certain embodiments, the mean curvature flow method grasps selected portions and types of topology of the surface shape of the blood vessel network 402. In certain embodiments, the selected portions can include or exclude geometric features of the surface shape. In certain embodiments, the selected portions can include or exclude "noisy" artifacts of the surface shape. In certain embodiments, the selected portions can include or exclude the entire topology of the surface shape. In certain embodiments, the second method grasps the topology of the surface shape of the blood vessel network 402 and ignores all or almost all "noisy" artifacts. In certain embodiments, the second method grasps the topology of the surface shape of the blood vessel network 402 and ignores all or almost all geometric features of the surface shape.

In certain embodiments, the virtual skeleton model 400 is created by the mean curvature method 410 grasping the topology of the blood vessel network 402 as well as essential geometric features of the blood vessel network 402. In certain embodiments, exemplary essential geometric features include big bulges, but ignores small geometric features of the blood vessel network including "noisy" artifacts. The resulting virtual skeleton model 400 is a skeleton of the blood vessel network 402 and is in a form of the graph 404.

In certain embodiments, the edges 310 that connect terminal points 308 represent center lines of surfaces of the blood vessel network 402. In certain embodiments, nodes or points 304 that belong to a single edge 310 represent terminal points 308. In certain embodiments, nodes or points 304 that belong to more than two edges 310 are represented as a bifurcation point 306. In certain embodiments, the graph 404 is broken into edge 310 based on the bifurcation points 306 within the graph 404.

Figure 5A:
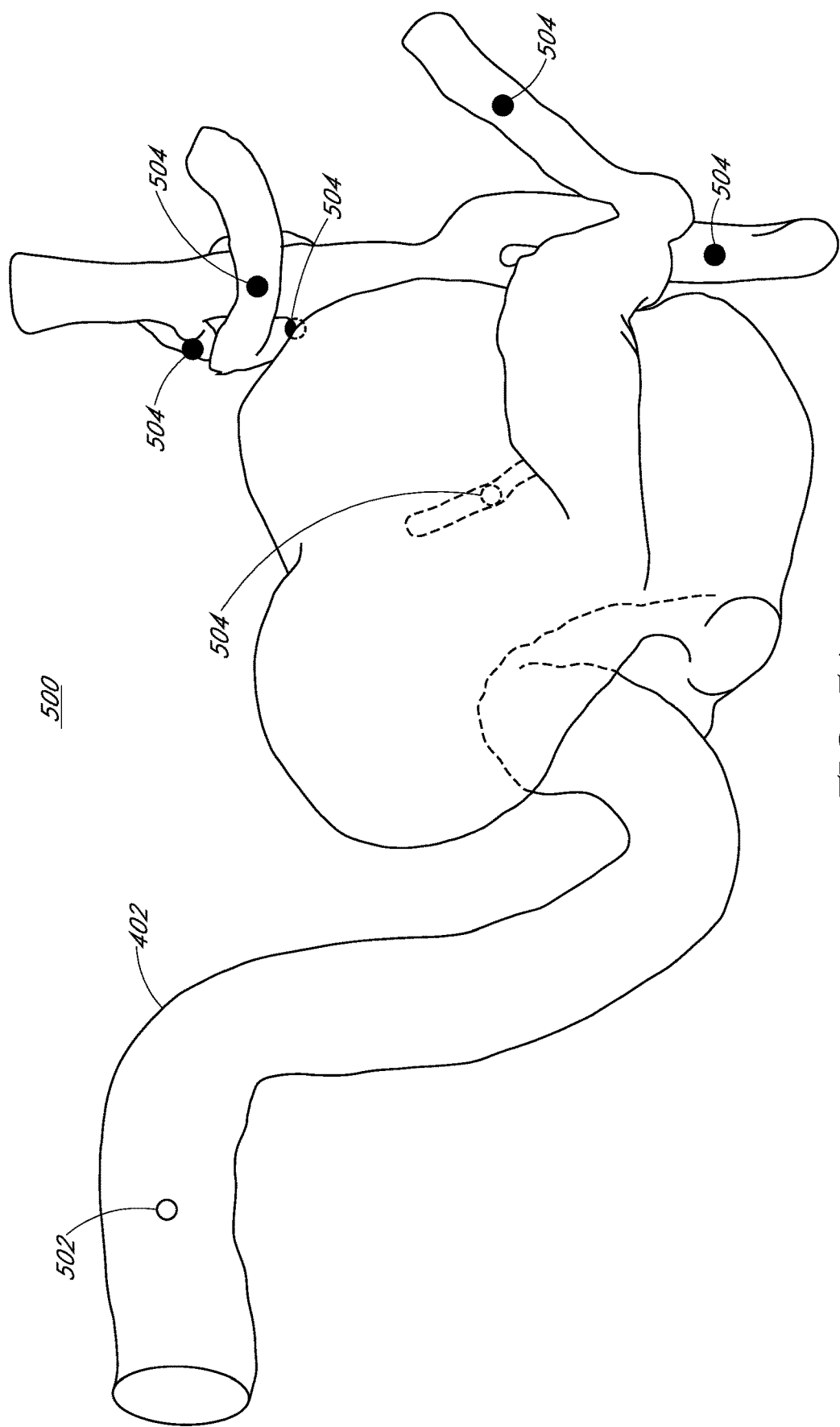
FIG. 5A illustrates a virtual inlet/outlet model of the blood vessel network illustrated in FIG. 4A.

FIG. 5A illustrates a virtual inlet/outlet model 500 of the blood vessel network 402 illustrated in FIG. 4A. The inlet/outlet module 104 illustrated in FIG. 1 is configured to identify inlet points 502 and outlet points 504 of the blood vessel network 402 within the virtual skeleton module 400 created by the skeletonization module 102. The inlets 502 and outlets 504 denote blood flow direction into and out of the virtual skeleton module 400 of the blood vessel network 402.

In certain embodiments, the identification of the inlets 502 and outlets 504 is performed automatically. In certain embodiments, the identification of the inlets 502 and outlets 504 is performed semi-automatically. In certain embodiments, the identification of the inlet 502 is performed semi-automatically while the identification of the outlet 504 is performed automatically. In certain embodiments, the identification of the outlet 504 is performed semi-automatically while the identification of the inlet 502 is performed automatically.

In certain embodiments, the inlet/outlet module 104 identifies the inlets 502 and outlets 504 based on geometry of the virtual skeleton model 400. For example, in certain embodiments, the inlet/outlet module 104 identifies inlets 502 and outlets 504 based at least in part on characteristics of the plurality of skeleton points 406 determined by the skeletonization module 102.

Exemplary methods for identifying an inlet 502 include a plane method and a default method. However, the method for identifying the inlet 502 is not limited to the recited methods and includes changes and modifications to the disclosed methods that would be known by a person having ordinary skill in the art.

The plane method can include identifying a cutting plane based on specific geometry of the surface mesh of the blood vessel network 402. In certain embodiments, the identified specific geometry are large, flat regions on the surface mesh of the blood vessel network 402. Once the cutting plane is identified, the inlets 502 are identified as terminal points 308 within a certain distance of the identified cutting plane and with r_avg>than a certain value. In certain embodiments, the distance is a range between any of 2 mm and 10 mm, 3 mm and 9 mm, 4 mm and 8 mm, 5 mm and 7 mm, and 6 mm. In certain embodiments, the distance is a value. The value can be 2 mm, 3 mm, 4 mm, 5 mm, 6 mm, 7 mm, 8 mm, 9 mm, or 10 mm. In certain embodiments, the certain value that r_avg is greater than any of 0.5 mm, 1 mm, 2 mm, 3 mm, 4 mm, 5 mm, 6 mm, 7 mm, 8 mm, 9 mm, and 10 mm. In certain embodiments, inlets 502 are identified as terminal points 308 that are within 5 mm of the cutting plane and with r_avg>1 mm.

The default method is employed when the plane method is unable to identify the inlets 502. For example, in cases where the terminal points 308 that are candidates for being an inlet 502 are outside the certain distance specified by the plane method, the default method ignores the certain distance requirement and identifies the terminal points 308 that are candidates for being an outlet point 504 as an inlet point 502. For example, if the plane method fails, any identified outlet 504 with r_avg>1 mm is considered an inlet 502. A window is presented on the display device 112 for the healthcare provider to provide user input 114. In this way, the healthcare provider accepts/makes changes to the inlets 502 before proceeding.

Exemplary methods for identifying the outlets 504 include identifying terminal points 308 on edges 310 that are identified by the skeletonization module 102 as having small skeleton aspect ratio according to the formula:

$$AR_s = \frac{r_{avg}}{L},$$

where $r_{avg}$ is the average distance to the blood vessel surface for the edge 310 and L is the length of the edge 310. However, the method for identifying the outlet 504 is not limited to the recited method and includes changes and modifications to the disclosed method that would be known by a person having ordinary skill in the art.

In certain embodiments, each skeleton point 406 of the plurality of skeleton points 406 is classified based on whether the skeleton point 406 is associated with one edge 310 within the virtual skeleton model 400 or with more than one edge 310 within the virtual skeleton model 400. In certain embodiments, skeleton points 406 associated with a single edge 310 are identified as terminal points 308 by the inlet/outlet module 104. The inlet/outlet module 104 classifies the terminal points 308 as an inlet 502 or an outlet 504 into the blood vessel network 402.

The edges 310 are generated through the virtual skeleton module 400 from the inlets 502 to the outlets 504. In certain embodiments, segmentation issues can arise in which loops or cycles 312 are incorrectly created within the virtual skeleton module 400. These incorrect loops or cycles 312 can occur due to a false connection between edges 310.

Figure 5B:
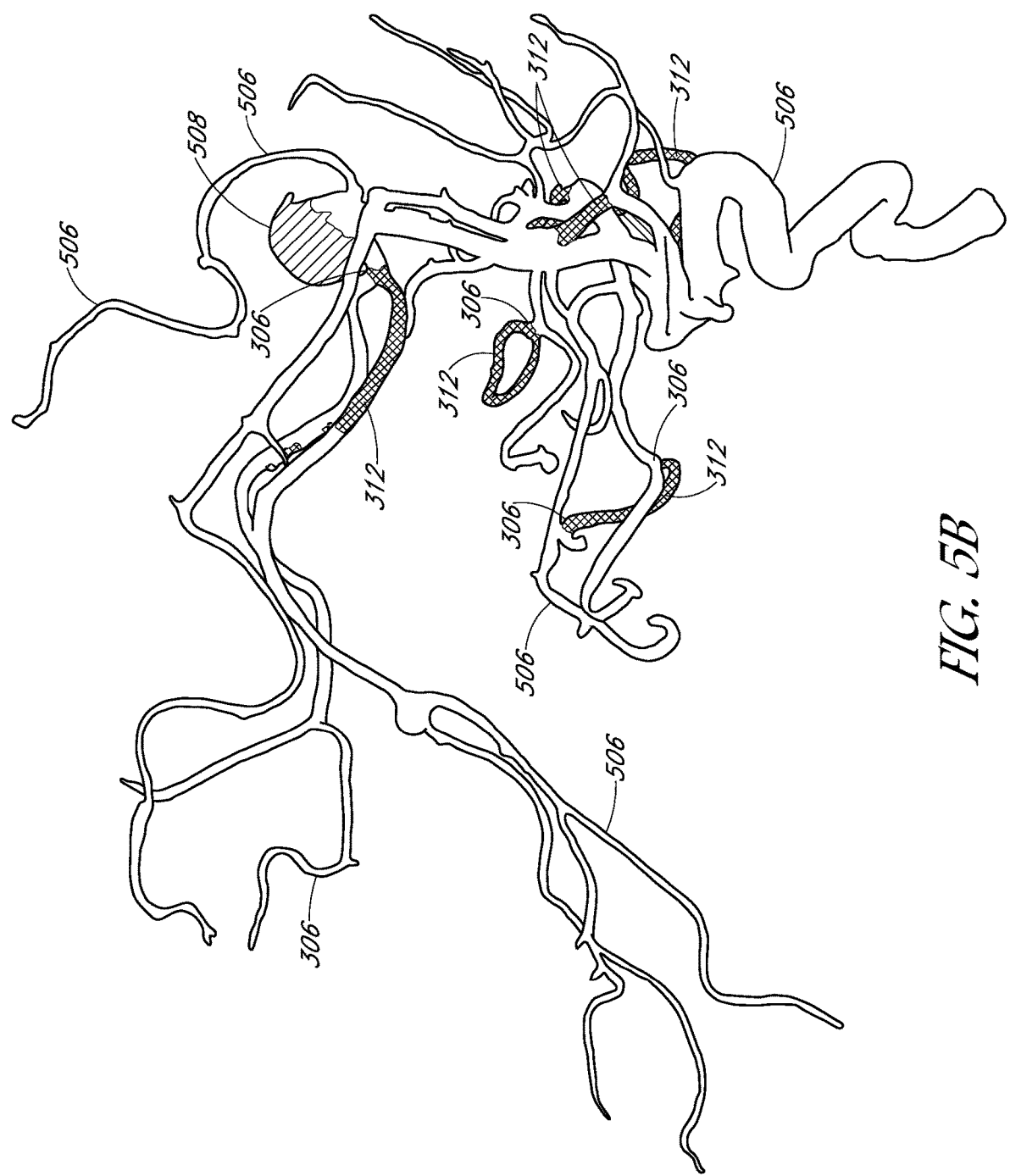
FIG. 5B illustrates the inlet/outlet module initially masking the blood vessel network as blood vessel, cycle, or potential aneurysm.

In certain embodiments as is illustrated in FIG. 5B, the blood vessel network 400 is initially masked by the inlet/outlet module 104 as blood vessel 506, cycle 312, or potential aneurysm 508.

Figure 6A:
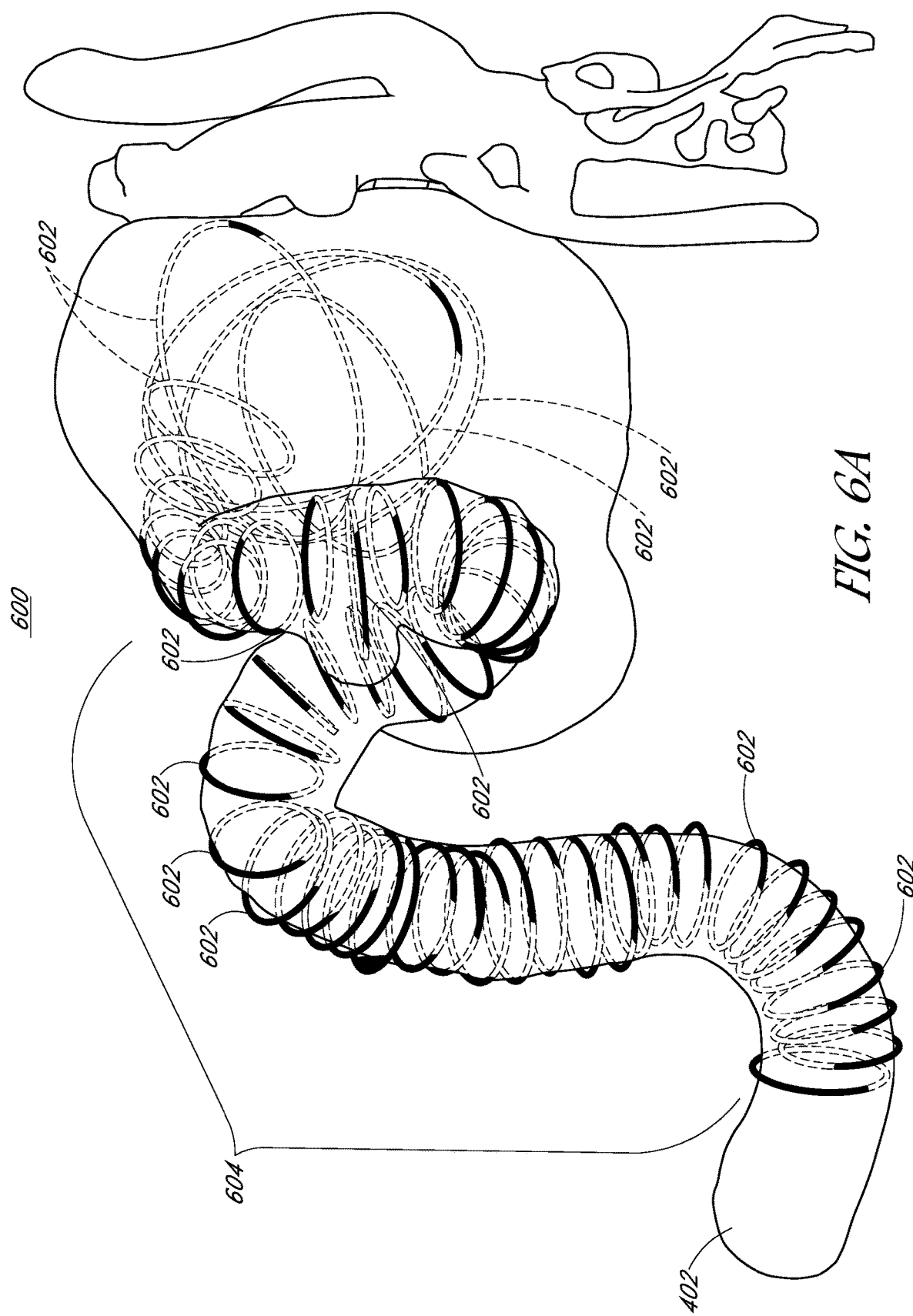
FIG. 6A illustrates the construction module fitting one or more predefined geometric shapes to the virtual skeleton model created by the skeletonization module to form an ellipse model.

As is illustrated in FIG. 6A, the construction module 106 fits one or more predefined geometric shapes to the virtual skeleton model 400 created by the skeletonization module 102. In the embodiment illustrated in FIG. 6A, the at least one predefined geometric shape is an ellipse 602 and forms an ellipse model 600. In certain embodiments, for each skeleton point 406 along the edge 310 an appropriately sized or effective ellipse 602 is fitted. In certain embodiments, for each skeleton point 406 along the edge 310, the appropriately sized effective ellipse 602 is fitted through the surface points 408 corresponding to the skeleton point 406. Of course, the method is not limited to constructing and fitting ellipses 602 and may include other shapes as well as combinations of different shapes.

A plurality of ellipses 602 fitted along a plurality of skeleton points 406 of the edge 310 together form an elliptically shaped tube 606. In FIG. 6A, the fitted ellipses 602 form the elliptically shaped tubules 606. Thus, the elliptically shaped tubules 606 are represented as a set of ellipses 602 along the edge 310. Of course, the method is not limited to forming elliptically shaped tubules 606 from a plurality of adjacent ellipses 602 and may include other shapes as well as combinations of different shapes.

In certain embodiments, the construction module 106 fits the ellipses 602 in a plane that is orthogonal to a tangent vector of the edge 310. In certain embodiments, the tangent vector is smoothed before defining the orthogonal plane. In certain embodiments, the smoothing is a one-step averaging smoothing.

Figure 6B:
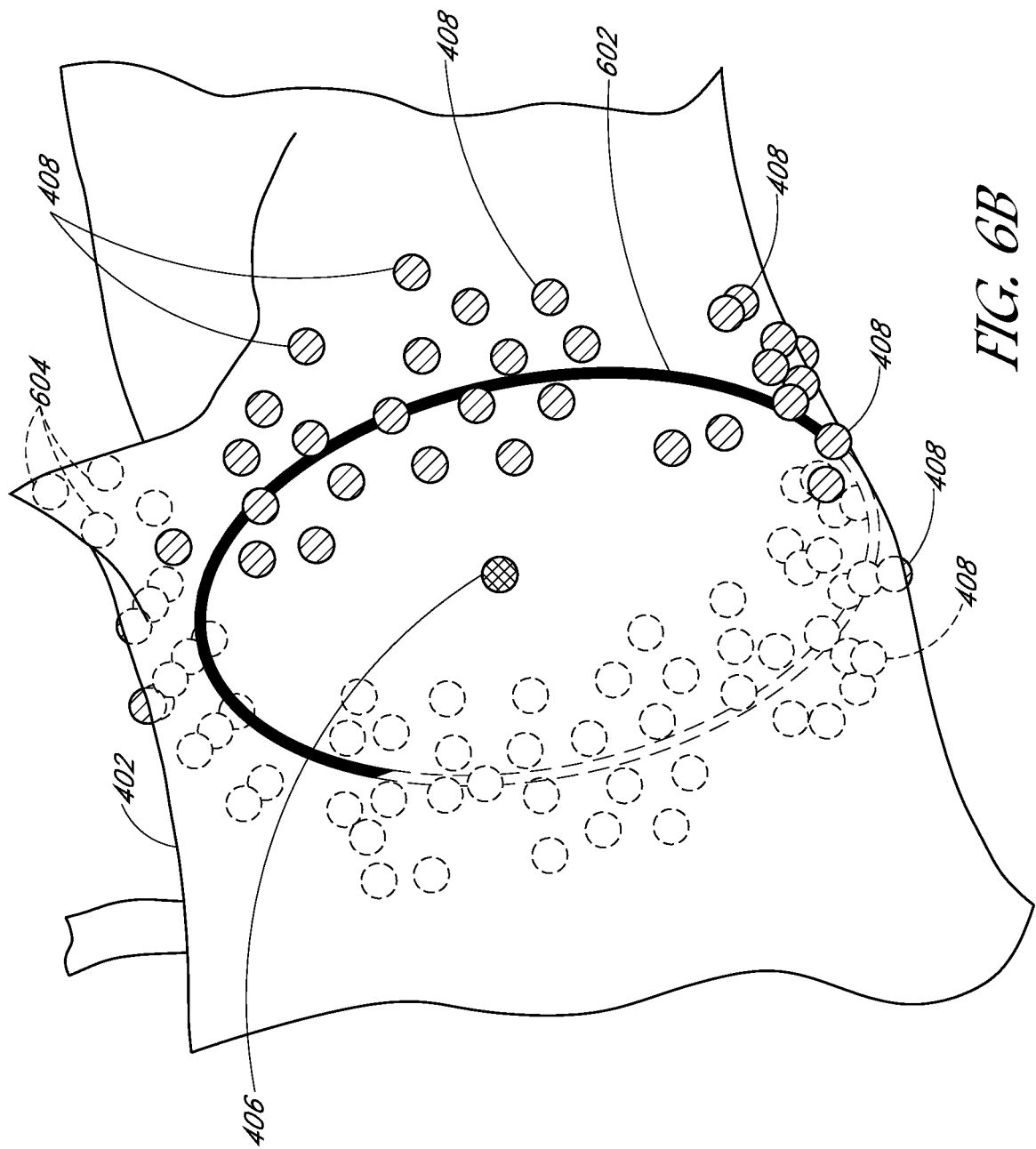
FIG. 6B illustrates the construction module fitting an ellipse to one of the skeleton points of the edge.

As is illustrated in FIG. 6B, the construction module 106 fits an ellipse 602 to one of the skeleton points 406 of the edge 310. The skeleton point 406 represents one or more of the surface points 408. In certain embodiments, the surface points 408 with high surface curvature values 604 are excluded by the construction module 106 when the construction module 106 fits the ellipse 602. The surface points 408 with high curvature values 604 may represent "noise" artifacts and not actual surface points 408 of the blood vessel network 402.

In certain embodiments, the construction model 106 determines statistics related to the one or more predefined geometric shapes fitted to the virtual skeleton model 400. In certain embodiments, the statistics are used by, for example, the filtering module 108. These statistics can include mean, minimum, maximum, and standard deviations for each of the one or more predefined geometric shapes fitted along each edge 310. Of course, these statistics are not limited to the listed statistics and can include other statistics that would be known by a person having ordinary skill in the art.

Figure 7A:
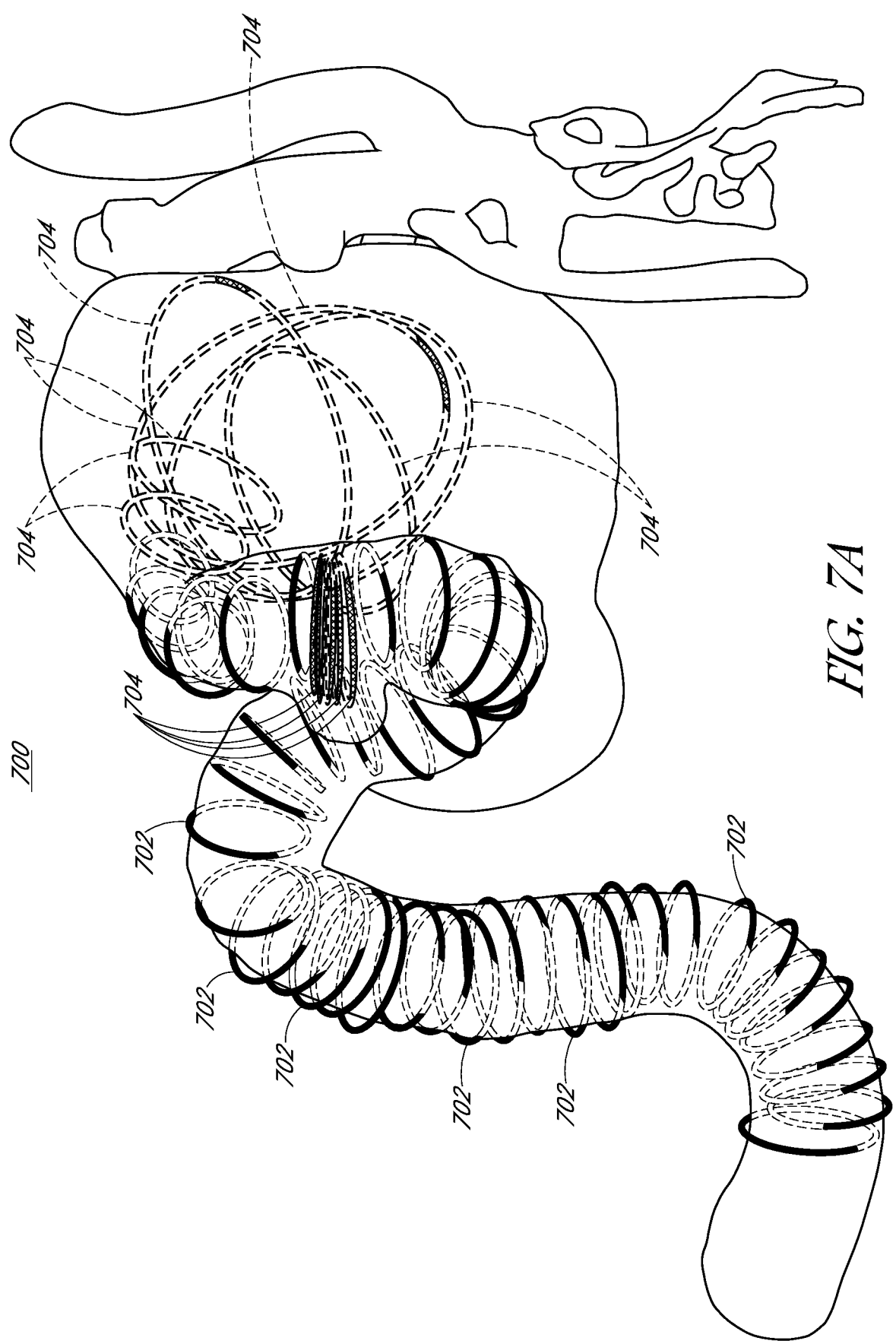
FIG. 7A illustrates the output of the filtering module represented by a filter model.
Figure 7B:
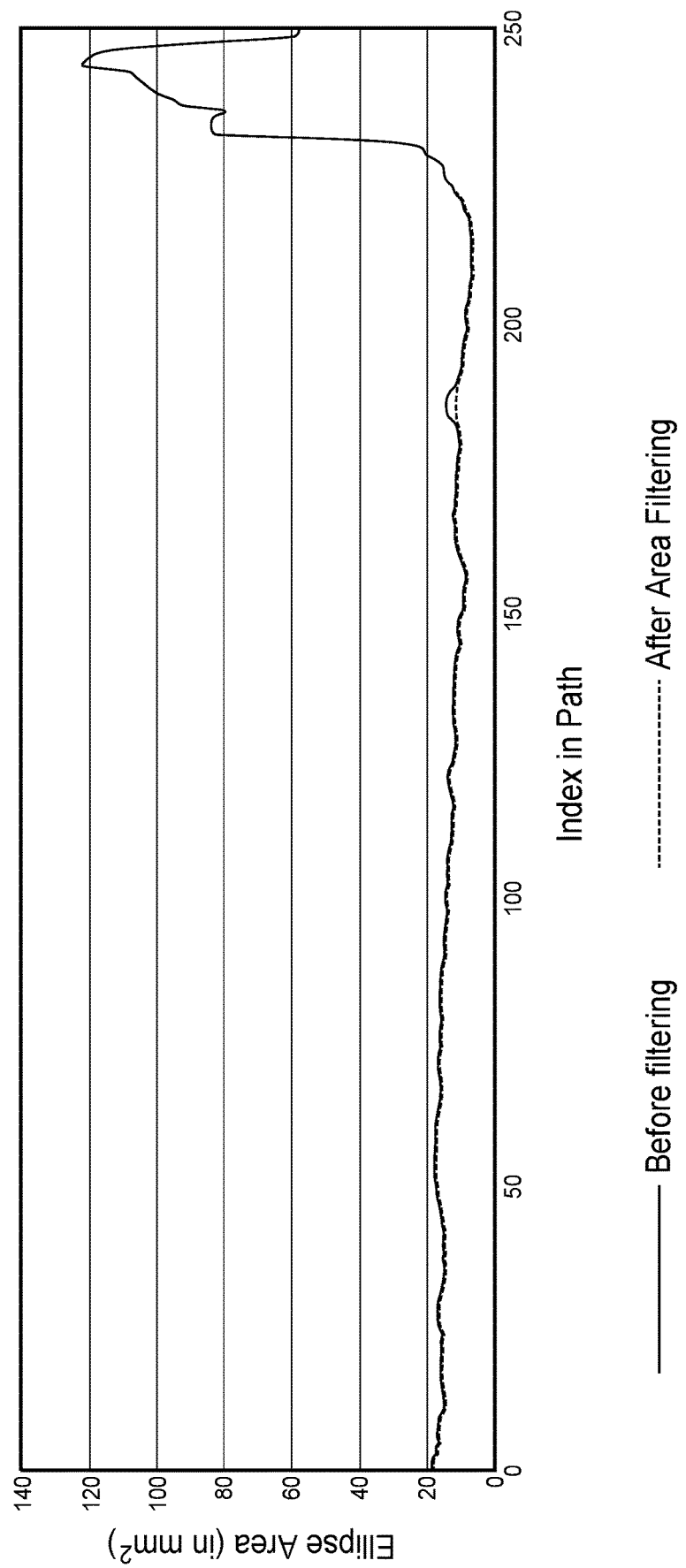
FIG. 7B illustrates values of ellipse areas associated with skeleton points at locations along the edge.

FIG. 7A illustrates the output of the filtering module 108 represented by a filter model 700. The filter model 700 in FIG. 7A is created by filtering the ellipse model 600 from FIG. 6A. In certain embodiments, the filtering module 108 is configured to further identify potential aneurysms 704 from the potential aneurysms 508 within the virtual skeleton model 400 of the blood vessel network 402. In certain embodiments, the filtering module 108 analyzes the one or more predefined geometric shapes, such as ellipses 602, fitted by the construction module 106 to the virtual skeleton model 400 along with one or more of the statistics generated for the one or more predefined geometric shapes, such as ellipses 602, determined by the construction model 106.

In certain embodiments, the one or more filtering steps are based on one or more of the statistics determined by the construction model 106. In certain embodiments, the filtering module 108 filters the virtual skeleton model 400 based on one or more statistics for each of the one or more predefined geometric shapes, such as ellipses 602, fitted at each skeleton point 406 along each edge 310. In certain embodiments, the one or more statistics include one or more of the mean, minimum, maximum, and standard deviations for each of the one or more predefined geometric shapes, such as ellipses 602. In certain embodiments, one or more of the steps within the one or more filtering steps are repeated or iterated to further identify one or more of the ellipses 602 as either a vessel ellipse 702 or a potential aneurysm 704 in the virtual skeleton model 400.

In certain embodiments, the one or more filtering steps include a step based on ellipse area statistics. FIG. 7B illustrates ellipse areas associated with skeleton points 406 along the edge 310. A first line in FIG. 7B is identified as "before filtering" and a second line is identified as "after area filtering". Notably, the after area filtering line does not include removed skeleton points 406 flagged as potential aneurysms 704. The after area filtering line includes only skeleton points 406 associated with healthy blood vessel network 402 or vessel ellipses 702.

In certain embodiments, for example, filtering based on an area of ellipse 602 statistics can include statistically filtering each skeleton point 406 along the edge 310 based on the areas of the ellipses 602 associated with the skeleton points 406 of the edge 310.

In certain embodiments, a skeleton point 406 within the virtual skeleton model 400 is flagged as a potential aneurysm 704 based on the area of the ellipse 602. For example, in certain embodiments, if $$A_i > A_{mean} + 2*A_{sd}$$

where $A_{mean}$ is the mean area for the edge 310 and $A_{sd}$ is the standard deviation then the skeleton point 406 is flagged as a potential aneurysm 704. Once the skeleton point 406 and the surface points 408 and ellipse 602 associated with the skeleton point 406 are flagged as a potential aneurysm 704 and not as a vessel ellipse 702, the skeleton point 406 is removed from the virtual skeleton model 400. In certain embodiments, for sufficiently long sections (>5 mm) of the edge 310, $A_{mean}$ is set using a linear regression, allowing it to reduce over the length of the section.

In certain embodiments, for skeleton points 406 and the surface points 408 and ellipses 602 associated with the skeleton points 406 that are not identified as potential aneurysms 704, the ellipses 602 associated with the skeleton points 406 are identified as vessel ellipses 702.

In certain embodiments, one or more constraints are placed on $A_{mean}$ to ensure that the areas of the ellipses 602 behave realistically over the entire path of the edge 310. The one or more constraints can relate to whether the skeleton point 406 is located at a junction within the virtual skeleton model 400. In certain embodiments, the junction is at a bifurcation point 306 or at a confluence within the virtual skeleton model 400.

In certain embodiments for bifurcation, the additional constraint is:

$$A_{mean} = \min(A_{mean}, 1.2 * A_{healthy}).$$

where $A_{healthy}$ is the previous healthy section mean. This ensures the overall trend is for the area to decrease.

In certain embodiments for confluences, the additional constraint is:

$A_{mean}$ is set based on the maximum $A_{healthy}$ of all the inlets 502. This prevents confluences from being flagged as false positives.

In certain embodiments, multiple passes of area filtering are performed on the skeleton points 406 and associated ellipses 602 to ensure that the final statistics represent the healthy blood vessel network 402 through that region.

In certain embodiments, edges 312 with $A_{max} < \pi$ mm$^2$ are statistically unlikely to contain aneurysms and are ignored.

Figure 8A:
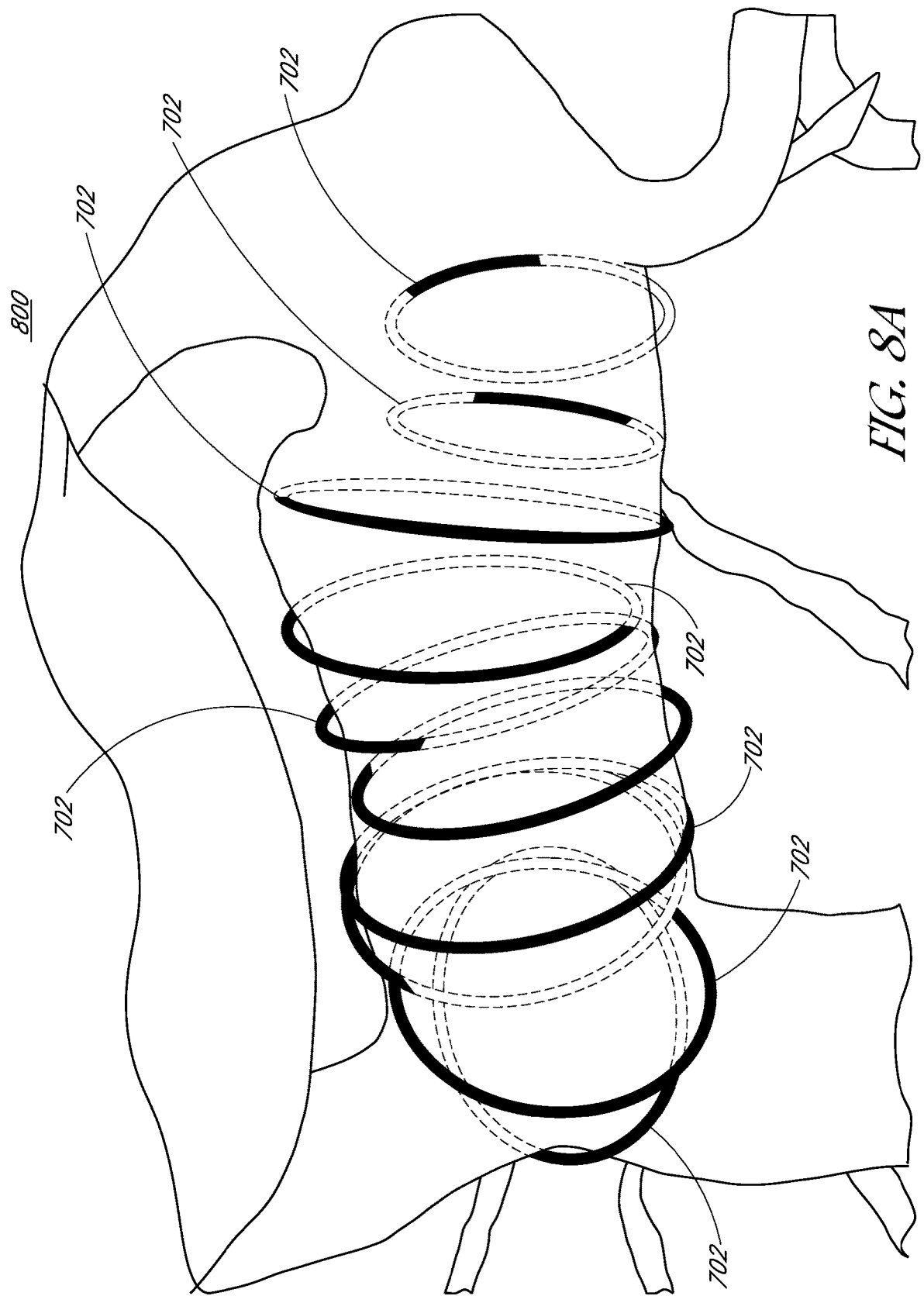
FIG. 8A illustrates the output of the filtering module after area filtering of the ellipse.

FIG. 8A illustrates the output of the filtering module 108 after area filtering of the ellipse 602. In FIG. 8A, the illustrated ellipses 602 have been flagged as vessel ellipses 702, not potential aneurysms 704.

Figure 8B:
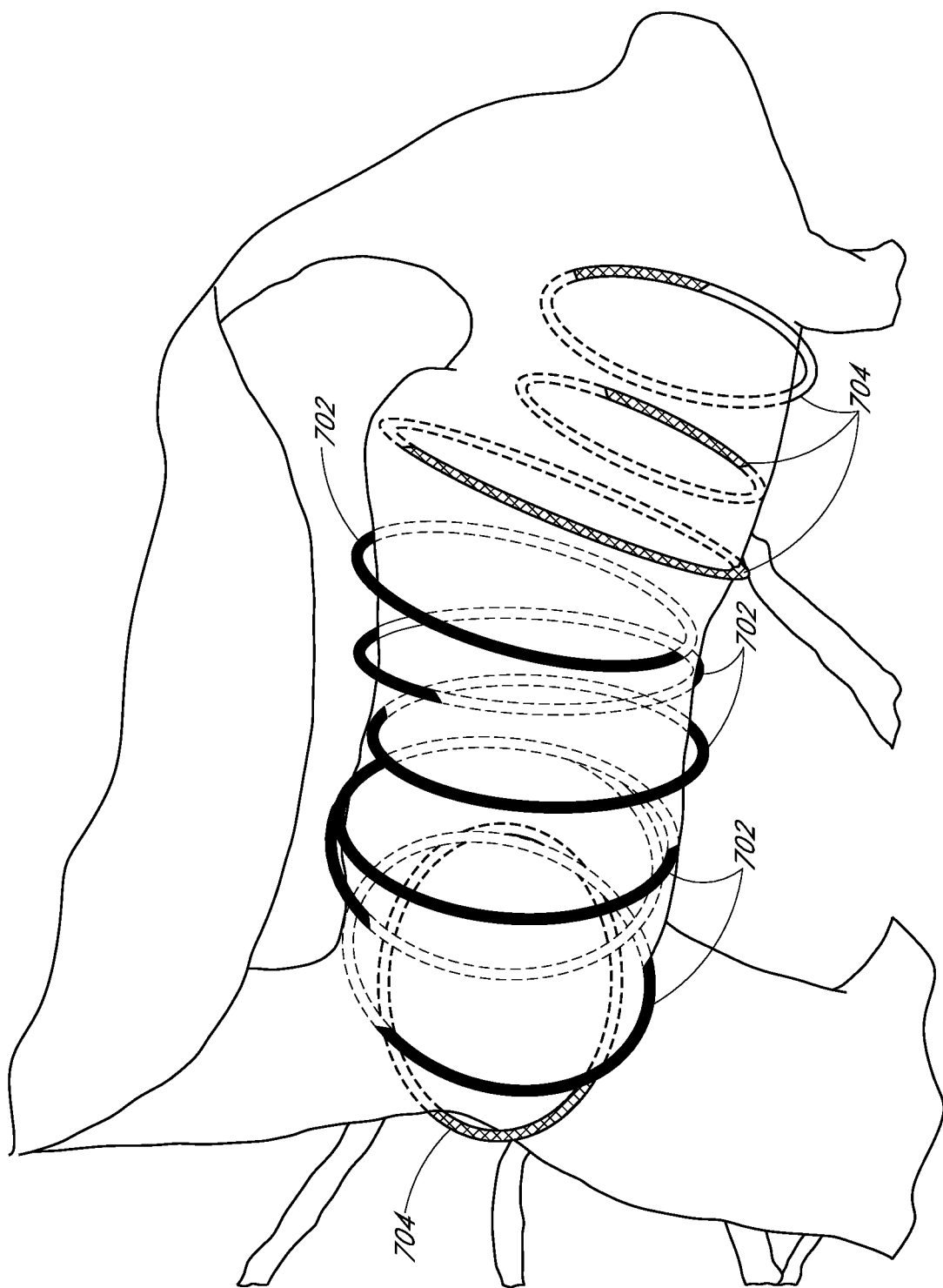
FIG. 8B illustrates the output of the filtering module after further filtering the output in FIG. 8A for variations in eccentricity of the ellipses.

FIG. 8B illustrates the output of the filtering module 108 after further filtering the output in FIG. 8A for variations in eccentricity. In certain embodiments, the additional pass of eccentricity filtering captures regions of high eccentricity that were not flagged during area filtering. As is illustrated in FIG. 8B, some of the ellipses 702 which were not flagged as potential aneurysms 704 in FIG. 8A based on variations in adjacent areas of ellipses 702, were flagged as having high variations in eccentricity between adjacent ellipses 702.

Thus, FIG. 8B illustrates in certain embodiments that the one or more filtering steps includes a step based on ellipse eccentricity statistics. For example, filtering based on eccentricity statistics of the ellipse 602 can include statistically filtering each edge 310 based on the ellipse eccentricity. Filtering based on ellipse eccentricity may identify a region of the virtual skeleton model 400 as a potential aneurysm 704. For example, even though the area of the adjacent ellipses 602 in FIG. 8A along the edge 310 do not vary enough for the filtering model 108 to flag the area as a potential aneurysm 704 based on ellipse area statistics, the filtering module 108 may flag the area based on variations in the eccentricity of the adjacent ellipses 602. The variation in the eccentricity may be indicative of a potential aneurysm 704 even though there is little deviation in the area across adjacent ellipses 602. In certain embodiments, the filtering module 108 determines the eccentricity of the ellipse 602 by the equation:

$$E = \frac{a}{b},$$

where a and b are the major and minor radii of the ellipse 602.

In certain embodiments, a skeleton point 406 within the virtual skeleton model 400 is flagged as a potential aneurysm 704 based on the eccentricity of the ellipse 602. In certain embodiments, the filtering module 108 removes the flagged skeleton points 406 from the virtual skeleton model 400 based on a comparison of the eccentricity calculated for the ellipse 602 and an eccentricity threshold value. In certain embodiments, the eccentricity threshold value is predetermined. In certain embodiments, the eccentricity threshold value is initially predetermined but then is updated based on measured data related to the blood vessel network 402.

In certain embodiments, the threshold eccentricity threshold value is any one of 1.1, 1.2, 1.3, 1.4, and 1.5. In certain embodiments, the filtering module 108 flags skeleton points 406 associated with an ellipse 602 with eccentricity that exceeds the eccentricity threshold value. For example, if the eccentricity of the ellipse 602 associated with a skeleton point 406 exceeds $E_i > 1.3$, the skeleton point 406 is removed from the virtual skeleton model 400 and identified as a potential aneurysm 704. In certain embodiments, the filtering pass by the filtering module 108 may also pick up very ovalized portions of the blood vessel network 402.

In certain embodiments, if the filtering module 108 determines that the ellipses 602 associated with skeleton points 406 along an edge 310 have eccentricity values that do not exceed a max threshold value, that edge 310 likely does not contain an aneurysm 704 and may be ignored. In certain embodiments, the max threshold value can be any one of 1.1, 1.2, 1.3, 1.4, 1.5, and 1.6. In certain embodiments, the max threshold value for the entire edge 310 is:

$$E_{max} < 1.4.$$

Figure 9A:
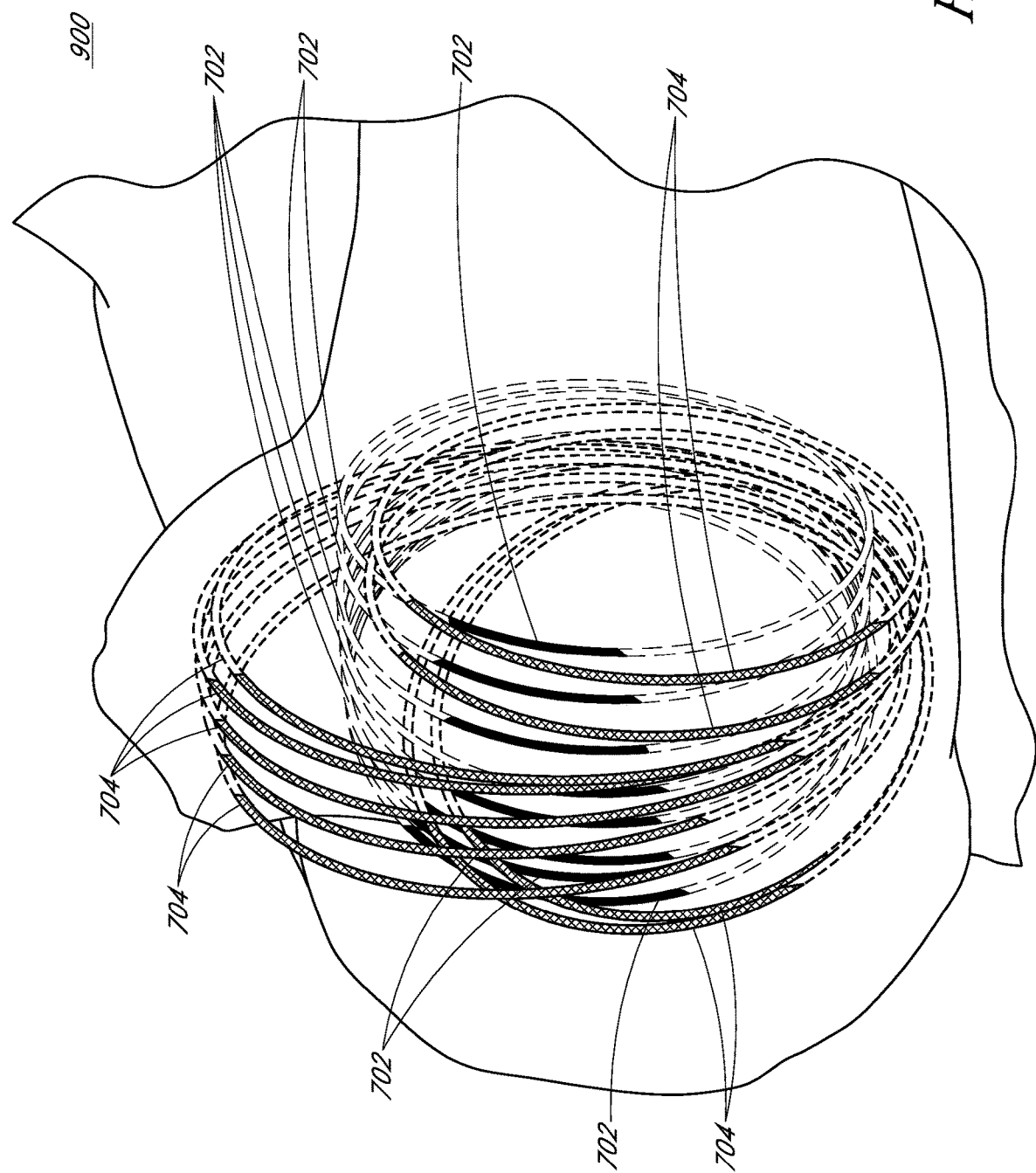
FIG. 9A illustrates the output of the filtering module after volume filtering of a first potential aneurysm.
Figure 9B:
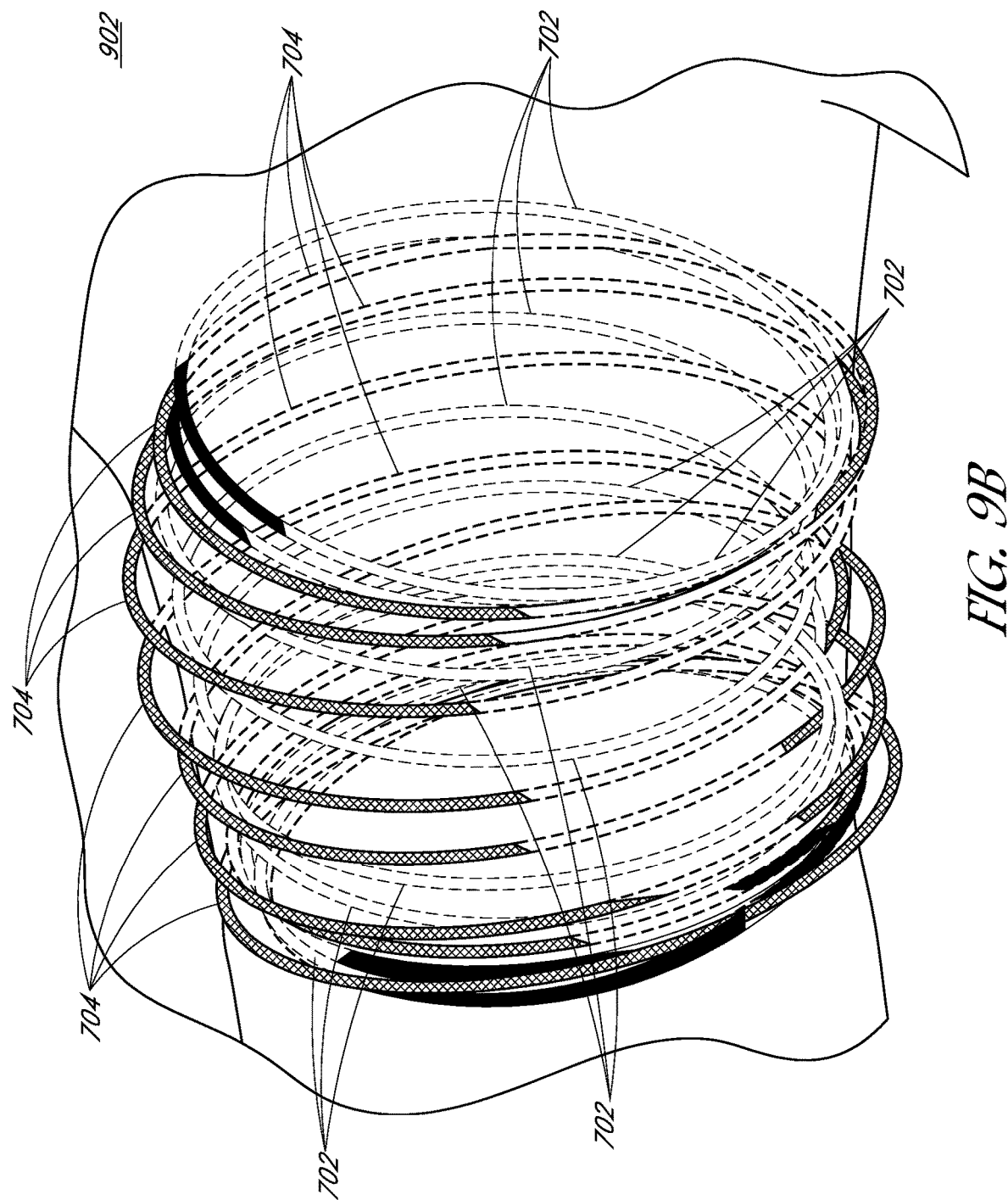
FIG. 9B illustrates the output of the filtering module after volume filtering of a second potential aneurysm.

FIG. 9A illustrates the output of the filtering module 108 after volume filtering of a first potential aneurysm 704. Volumetric filtering demonstrates the first potential aneurysm 704 is a true positive aneurysm 900. FIG. 9B illustrates the output of the filtering module 108 after volume filtering of a second potential aneurysm 704. Volumetric filtering demonstrates the second potential aneurysm 704 is a false positive aneurysm 902.

In certain embodiments, the one or more filtering steps includes a step for filtering the skeleton points 406 that have been identified as potential aneurysms 704 and removed from the virtual skeleton model 400 by the filtering module 108. In certain embodiments, the potential aneurysms 704 were identified by the filtering module 108 during the filtering step based on ellipse area statistics (FIGS. 7A and 7B) and/or during the filtering step based on ellipse eccentricity statistics (FIGS. 8A and 8B). In this way, the filtering module 108 filters out false positive identified by the filtering module 108 during the filtering step based on ellipse area statistics and/or during the filtering step based on ellipse eccentricity statistics.

In certain embodiments, the filtering module 108 determines one or more volumes. The filtering module 108 determines one or more volumes related to the potential aneurysms 704. In certain embodiments, the filtering module 108 compares the volume of a healthy vessel in the region of the potential aneurysms 704 with the volume of the potential aneurysms 704.

In certain embodiments, the filtering module 108 computes a cylindrical volume using the ellipse areas 704 in the region of the potential aneurysm 704 to represent the volume of the potential aneurysm 704. In certain embodiments, the filtering module 108 computes a cylindrical volume in the region of the potential aneurysm 704 by interpolating the areas of the ellipses 702 on the sides of the potential aneurysm 704 into the region of the potential aneurysm 704. In this way, the interpolated volume represents the virtual volume of a healthy vessel in the area of the potential aneurysm 704.

In certain embodiments, the comparison between the cylindrical volumes indicates whether the potential aneurysm 704 is a true positive 900 or is a false positive 902. In certain embodiments, if the volume of the potential aneurysm 704 is not more than 15% greater than the virtual volume of the healthy vessel in the region of the potential aneurysm 704 then the potential aneurysm 704 is a false positive 902. In certain embodiments, if the volume of the potential aneurysm 704 is not more than 10% greater than the virtual volume of the healthy vessel in the region of the potential aneurysm 704 then the potential aneurysm 704 is a false positive 902. In certain embodiments, if the volume of the potential aneurysm 704 is not more than 5% greater than the virtual volume of the healthy vessel in the region of the potential aneurysm 704 then the potential aneurysm 704 is a false positive 902. In certain embodiments, the filtering module 108 applies the equation:

$V_e < 1.1 * V_h$, where $V_e$ is potential aneurysm volume, $V_h$ is healthy virtual volume.

The filtering module 108 compares the volumes and identifies the potential aneurysm 704 as a false positive 902 if the volumes satisfy the equation.

In certain embodiments, if the calculated volume of the potential aneurysm 704 is less than the equation:

$V_e < \pi$ mm$^3$, the potential aneurysm 704 is considered too small to represent a true positive 900 and is identified as a false positive 902.

Aneurysm Measurements

Figure 10A:
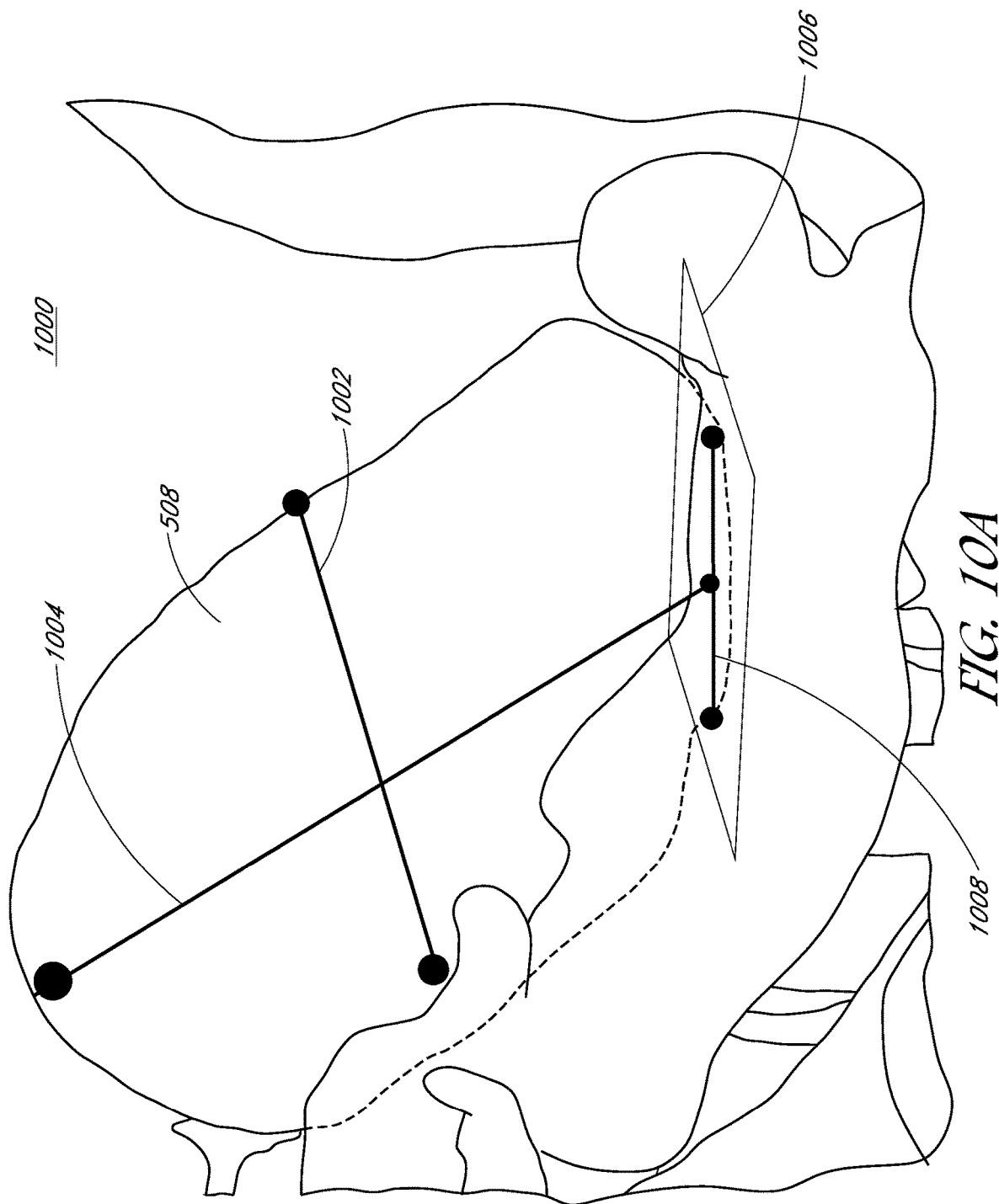
FIG. 10A illustrates idealized saccular measurements of a potential aneurysm.
Figure 10B:
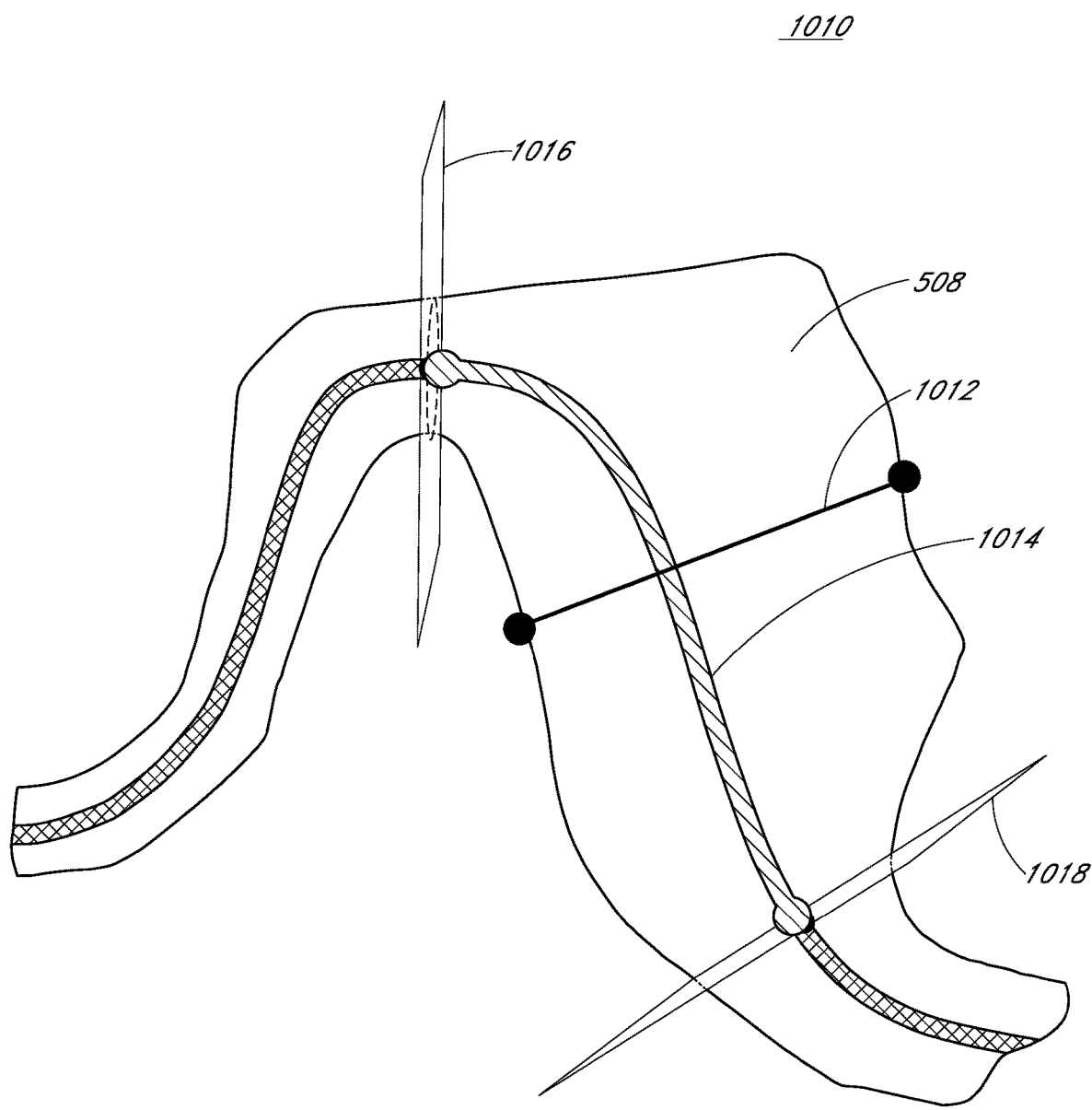
FIG. 10B illustrates idealized fusiform measurements of a potential aneurysm.

FIG. 10A illustrates idealized saccular measurements 1000 of a potential aneurysm 508. FIG. 10B illustrates idealized fusiform measurements 1010 of a potential aneurysm 508. In certain embodiments after the detection steps are performed, identified potential aneurysms 508 are shown in the display device 112 for final selection by the healthcare provider. The healthcare provider screens out false positives 902 from the list of potential aneurysms 508 using the user input 114. In certain embodiments, there are no more than a few false positives 902 per case and those false positives 902 are easily screened out by the healthcare provider via the display device 112. In certain embodiments, the user input 114 allows the healthcare provider to adjust the type of aneurysm (fusiform or saccular) for the aneurysms selected.

In certain embodiments as is illustrated in FIG. 10A, saccular form measurements 1000 include automatic neck-plane identification 1006, neck width 1008, dome height 1004, and dome width 1002.

In certain embodiments as is illustrated in FIG. 10B, fusiform form measurements 1010 include automatic distal 1016 and proximal plane 1018 identification, fusiform length 1014, and fusiform width 1012.

Aneurysm Comparison

Figure 11A:
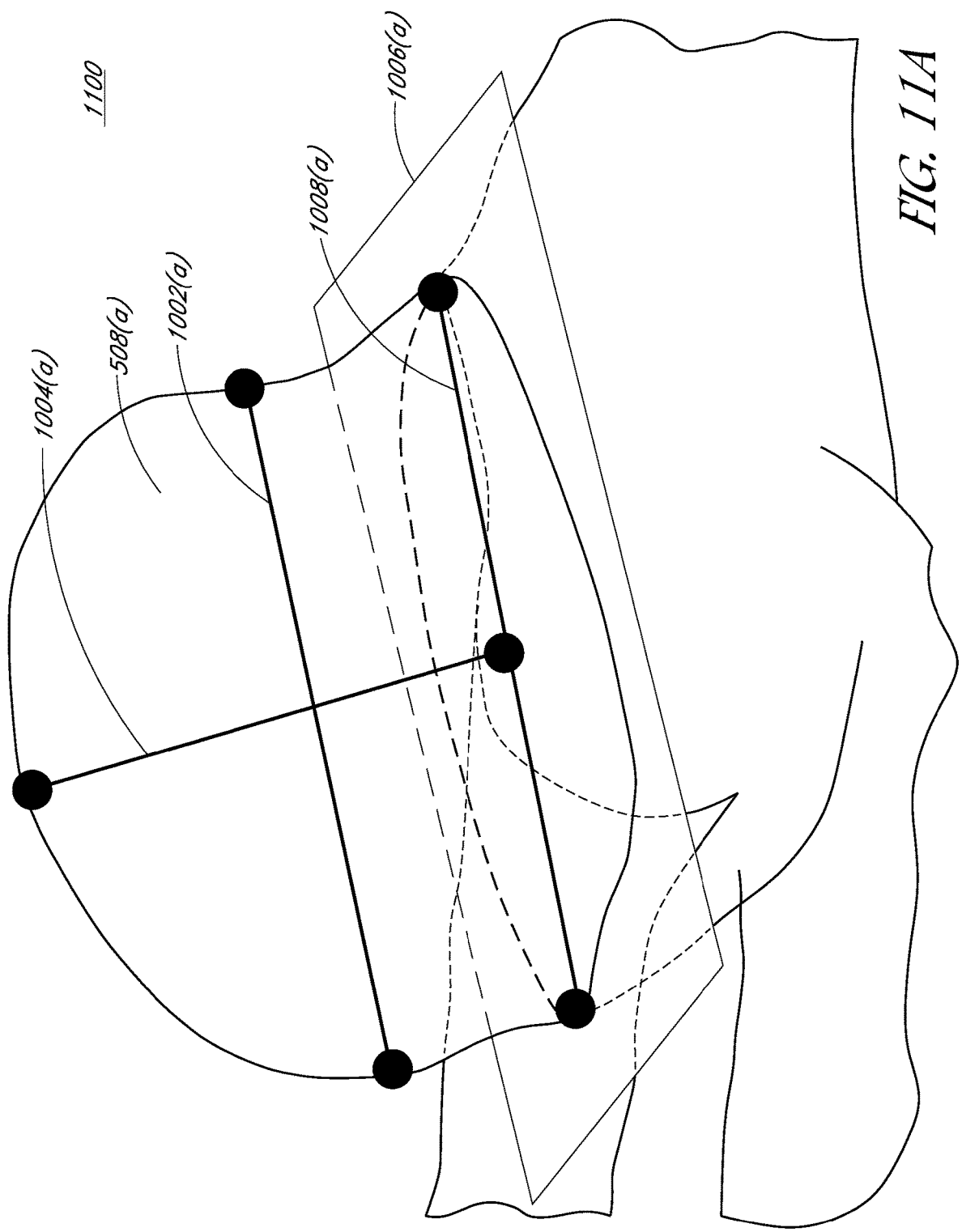
FIGS. 11A and 11B illustrate changes in dimensions of a saccular aneurysm over time.
Figure 11B:
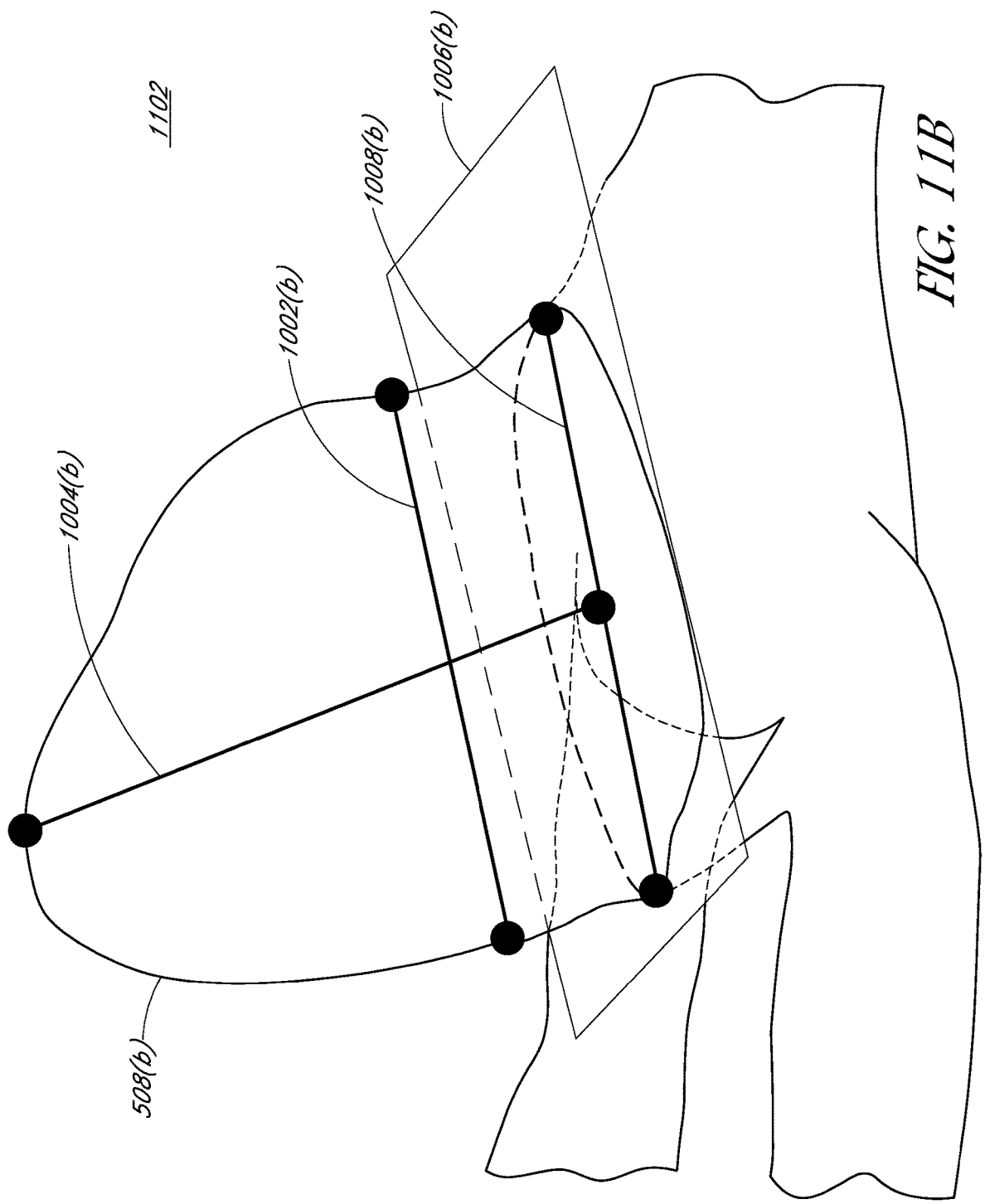
Figure 11C:
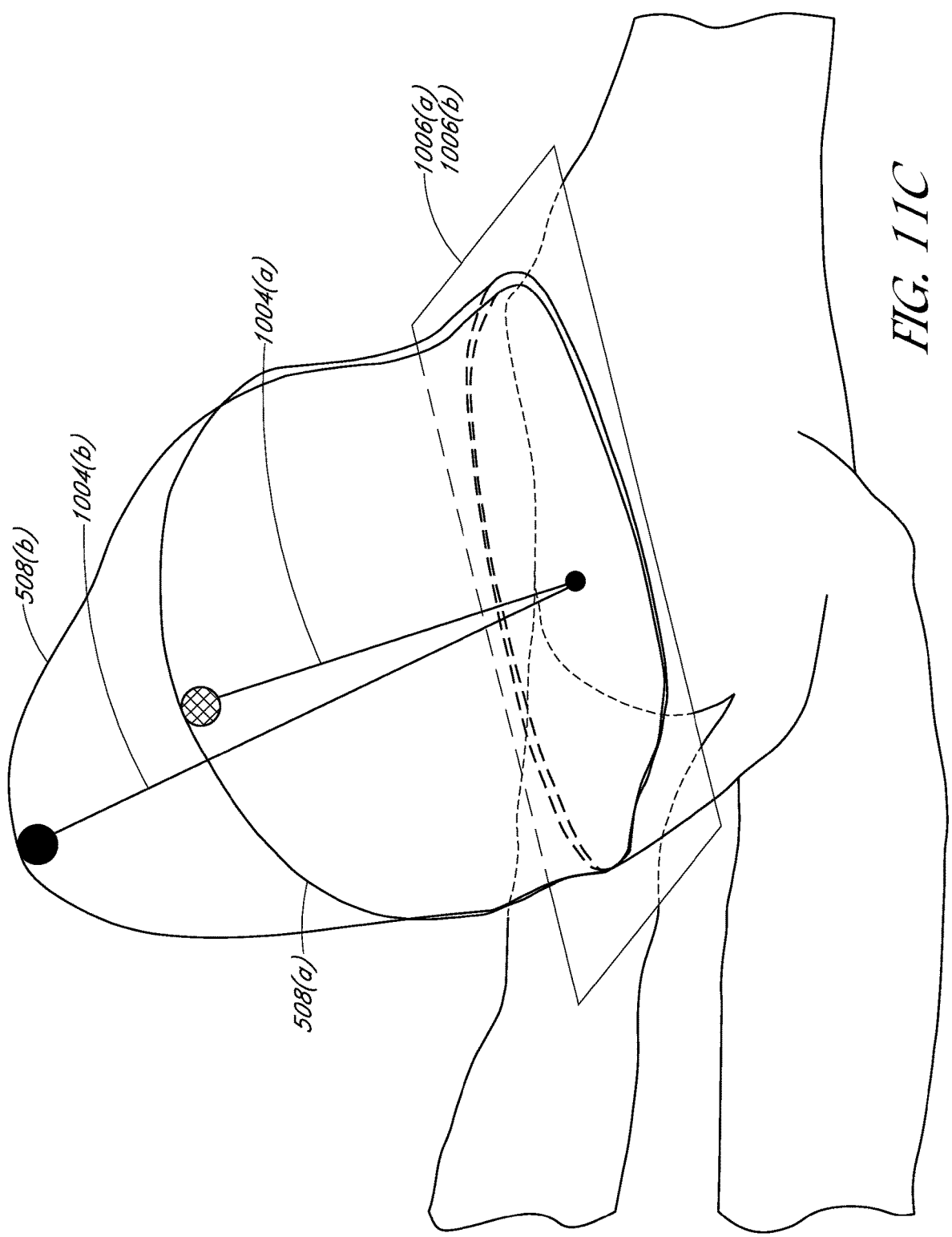
FIG. 11C illustrates the same identified aneurysm from FIGS. 11A and 11B overlapped to show growth of the identified aneurysm.

FIGS. 11A and 11B illustrate changes in dimensions of a saccular aneurysm over time. The scan illustrated in FIG. 11B is of the same identified aneurysm 508(a), 508(b) illustrated in FIG. 11A but after a period of time. FIG. 11C illustrates the same identified aneurysm 508(a), 508(b) from scans taken at different times overlapped to show growth of the identified aneurysm 508(a), 508(b). In certain embodiments as is illustrated in FIG. 11A, saccular form measurements 1100 include automatic neck-plane identification 1006(a), neck width 1008(a), dome height 1004(a), and dome width 1002(a). In certain embodiments as is illustrated in FIG. 11B, saccular form measurements 1102 include automatic neck-plane identification 1006(b), neck width 1008(b), dome height 1004(b), and dome width 1002(b).

A comparison between FIGS. 11A and 11B of the two scans of the same identified aneurysm 508(a), 508(b) shows growth in the identified aneurysm 508(a), 508(b) occurring over time. Given multiple scans of the same identified aneurysm 508(a), 508(b) taken over a period of time, the healthcare provider can track and monitor growth of the aneurysm 508(a), 508(b).

In certain embodiments, some features of the virtual skeleton model 400 created by the skeletonization module 102 will remain relatively constant, even if the positions, orientations, or extent of vasculature differ between the segmentations. In certain embodiments, these constant features include bifurcation points 306 and graph structure. Of course, features of the virtual skeleton model 400 that are relatively constant, such as terminal points 308, edges 310, cycles 312, and vertices 314 can also be used to orient the identified aneurysm 508(a), 508(b) fall within the scope of this disclosure. In certain embodiments, these features are used to orient the two geometries of the two scans of the same identified aneurysm 508(a), 508(b) with respect to one another. After the geometries are oriented, the identified aneurysms 508(a), 508(b) from each geometry are matched and measurements are compared.

Figure 12A:
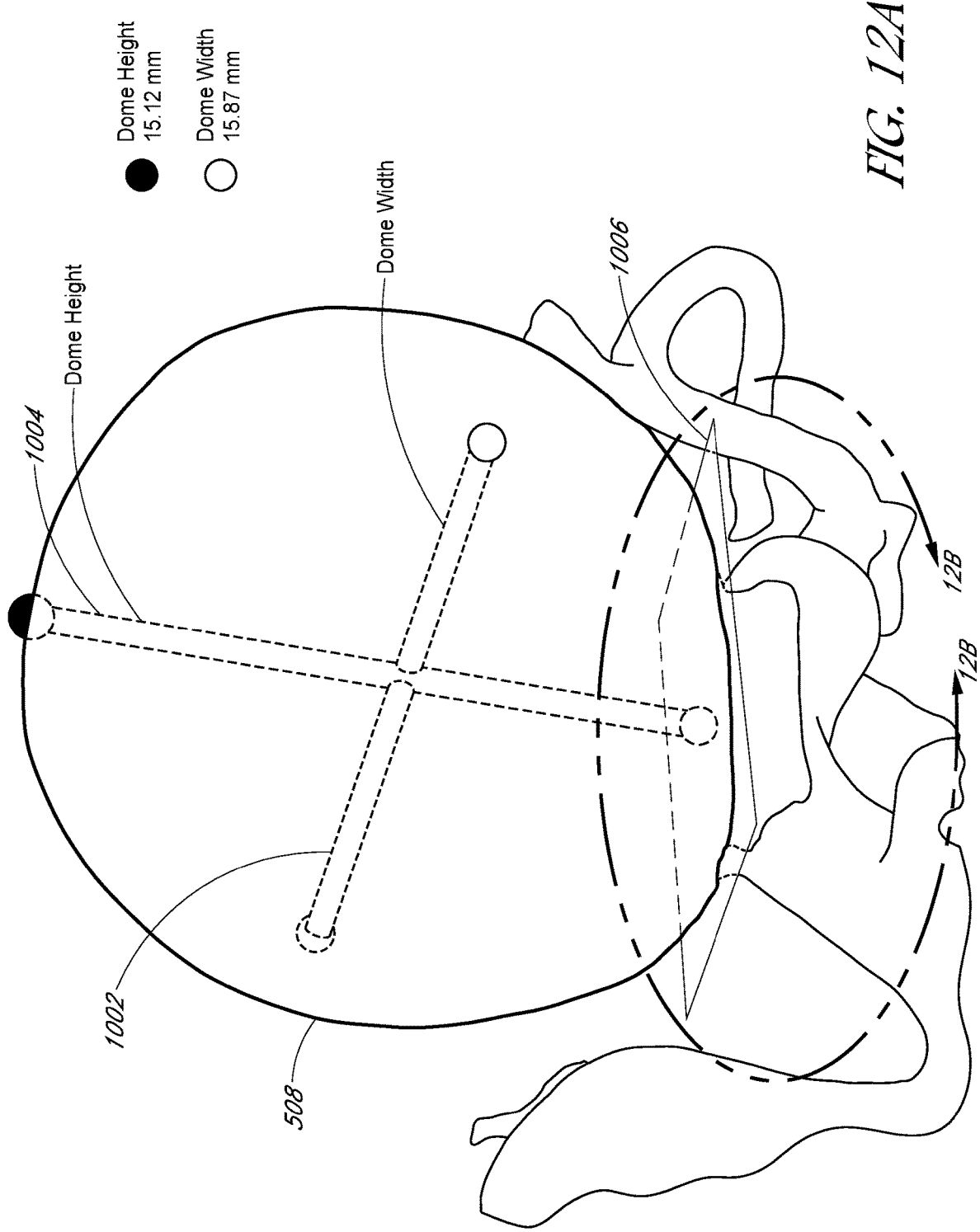

FIGS. 12A and 12B illustrate exemplary measurements and dimensions of a saccular aneurysm. The neck plane 1006 is defined as a best fit plane that encompasses the boundary between the aneurysmal sac and the parent vessel. As is illustrated in FIG. 12B, in certain embodiments, the neck plane 1006 is fitted on a set of "neck" points 1202 on a surface of the saccular aneurysm. Neck points 1202 with negative Gaussian curvature are given additional weight proportional to the magnitude of the Gaussian curvature to define the location of the neck plane 1006. The degree of curvature of each neck point is reflected by a color of the neck point 1202 in FIG. 12B.

The dome height 1004 is defined as a maximum distance between a center of the neck plane 1006 and a surface point on the aneurysmal sac of the aneurysm 508. The dome width 1002 is defined as a maximum width of the identified aneurysm 508 measured perpendicular to the line defining the dome height 1004.

Figure 13:
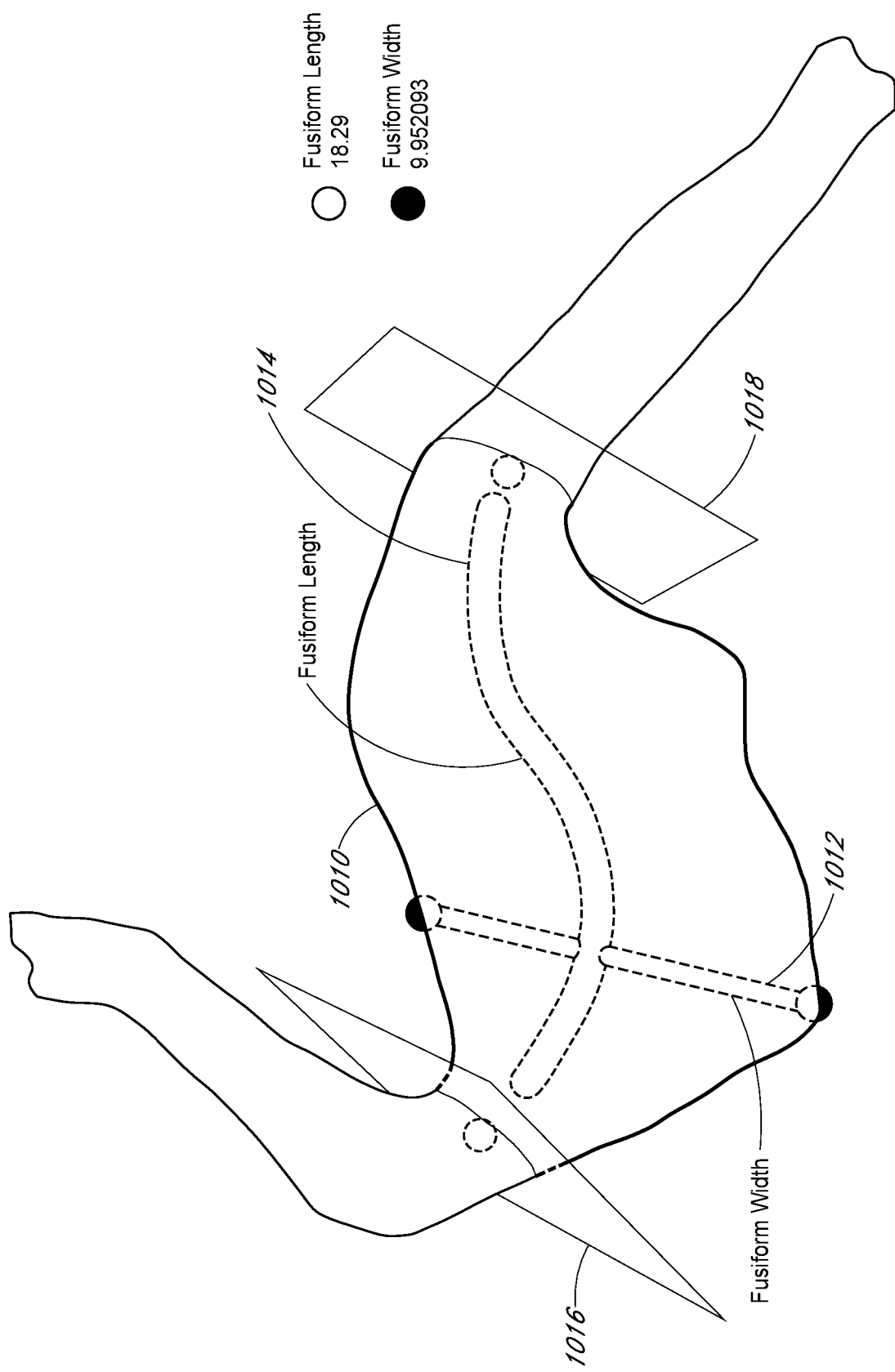
FIG. 13 illustrates exemplary measurements and dimensions of a fusiform aneurysm.

FIG. 13 illustrates exemplary measurements and dimensions of a fusiform aneurysm. A distal plane 1016 is defined as a plane positioned along the edge 310 or centerline that defines the fusiform aneurysm. The location of the distal plane 1016 is fitted in a similar way as the neck plane 1006 is fitted for the saccular aneurysm illustrated in FIG. 12B. A proximal plane 1018 is defined as a plane positioned along the edge 310 or centerline that defines the fusiform aneurysm. The location of the proximal plane 1018 is fitted in a similar way as the neck plane 1006 is fitted for the saccular aneurysm illustrated in FIG. 12B.

A length 1014 of the fusiform aneurysm is measured along the edge 310 of the virtual skeleton model 400 between the distal plane 1016 and the proximal plane 1018. In certain embodiments, the path points undergo several iterations of moving average smoothing to produce a more direct path than the virtual skeleton model 400.

A width 1012 of the fusiform aneurysm is measured perpendicular to the smoothed path between the distal plane 1016 and the proximal plane 1018.

Figure 14:
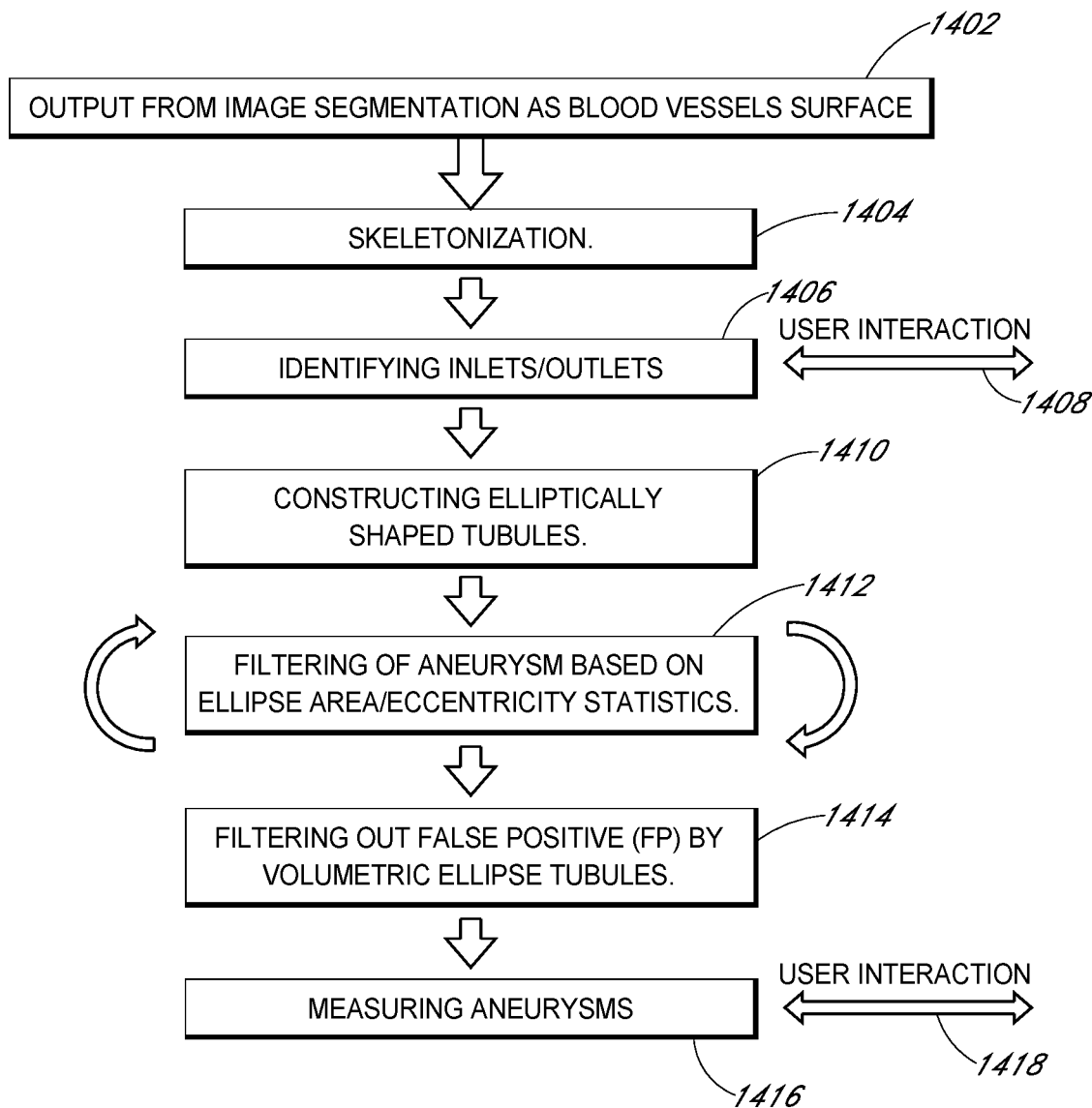
FIG. 14 illustrates a method for cerebral aneurysm detection performed by the computer system illustrated in FIG. 1.

FIG. 14 illustrates a method for cerebral aneurysm detection performed by the computer system 100 illustrated in FIG. 1. The process begins at step 1402 where the image apparatus 110 performs image segmentation and outputs blood vessel surfaces of the blood vessel network 402. The image apparatus 110 determined, analyzed, and/or displays vascular information for a patient. In certain embodiments, the image apparatus 110 is a Computed Tomography (CT) or Magnetic Resonance (MR) apparatus. In certain embodiments, the image apparatus 110 produces 3D image data or scans for the patient. In some examples, this data is in the form of a series of cross-sectional data scans. This data is represented, for instance through a process of resampling or other form of image processing. In certain embodiments, the image apparatus 110 from FIG. 1 provides the images used to create the model of the blood vessel network 402. In certain embodiments, images provided by the image apparatus 110 provide different geometric points of view of the blood vessel network 402

The method continues to step 1404 where the skeletonization module 102 skeletonizes the blood vessel surfaces of the blood vessel network 402. In certain embodiments, the computer system 110 provides the 3D image data or scans to the skeletonization module 102 for further processing. The skeletonization module 102 creates the virtual skeleton model 400 from the blood vessel network 402 of the patient. Once created and in certain embodiments, the virtual skeleton module 400 represents some or all of the geometric features of the blood vessel network 402. In certain embodiments, the virtual skeleton module 400 represents a subset of the geometric features of the blood vessel network 402.

In certain embodiments, the virtual skeleton model 400 is represented by a graph 404. In certain embodiments, the graph 404 is a mathematical structure used to model pairwise relations between objects that represent geometric features of the blood vessel network 402. In certain embodiments, the virtual skeleton model 400 represents at least a portion of the blood vessel network 402.

From the model of the blood vessel network 402, the skeletonization module 102 creates the virtual skeleton model 400. In certain embodiments, the virtual skeleton model 400 represents the entire blood vessel network 402. For example, the virtual skeleton model 400 can represent the blood vessel network 402 of the entire body of the patient. In certain embodiments, the virtual skeleton model 400 captures the topology and major geometry of the entire blood vessel network 402 including any potential aneurysm present in the entire blood vessel network 402. In certain embodiments, the virtual skeleton model 400 represents a subset of the blood vessel network 402. In certain embodiments, the virtual skeleton model 400 represents the blood vessel network 402 in a targeted region of the body. For example in certain embodiments, the virtual skeleton model 400 represents the blood vessel network 402 in the brain.

In certain embodiments, the virtual skeleton model 400 represents not only healthy blood vessels but also unhealthy blood vessels. In this way, the virtual skeleton model 400 includes unhealthy blood vessels, such as a potential aneurysm, to create a complete virtual skeleton model 400 of the blood vessel network 402.

The method continues to step 1406 where the inlet/outlet module 104 identifies inlets 502 and outlets 504 of the vasculature within the virtual skeleton model 400 created by the skeletonization module 102. The inlets 502 and outlets 504 denote blood flow direction into and out of the virtual skeleton model 400 of the vasculature. In certain embodiments, the identification of the inlets 502 and outlets 504 is performed automatically. In certain embodiments, the identification of the inlets 502 and outlets 504 is performed semi-automatically.

In certain embodiments, the inlet/outlet module 104 identifies the inlets 502 and outlets 504 based on geometry of the virtual skeleton model 400. For example, in certain embodiments, the inlet/outlet module 104 identifies inlets 502 and outlets 504 based at least in part on characteristics of the plurality of skeleton points 406 determined by the skeletonization module 102.

The method continues to step 1408 where a user may interact with the computer system 100 via the display device 112. Further, the user may repetitively interact with the display device 112 regarding the proposed selections of the inlets 502 and outlets 504 by the computer system 100. In this way, the healthcare provider confirms or re-selects the inlets 502 and/or outlets 504.

The method continues to step 1410 where the construction module 106 fits one or more predefined geometric shapes to the virtual skeleton model created by the skeletonization module 102. In certain embodiments, the construction module 106 is configured to fit the one or more predefined geometric shapes to each edge 310 created by the skeletonization module 102. In certain embodiments, at least one of the predefined geometric shapes is an ellipse 602. Of course the method is not limited to constructing and fitting ellipses 602 and may include other shapes as well as combinations of different shapes.

In certain embodiments, the construction module 106 fits the ellipses 602 in a plane that is orthogonal to a tangent vector of the edge 310. In certain embodiments, the tangent vector is smoothed before defining the orthogonal plane. In certain embodiments, the smoothing is a one-step averaging smoothing.

The method continues to step 1412. At step 1412, the filtering module 108 identifies potential aneurysms 508 within the virtual skeleton model 400 of the blood vessel network 402. In certain embodiments, the filtering module 108 analyzes the one or more predefined geometric shapes fitted by the construction module 106 to the virtual skeleton model 400 along with one or more of the statistics generated for the one or more predefined geometric shapes determined by the construction model 106.

In certain embodiments, the filtering module 108 performs one or more filtering steps to the virtual skeleton model 400 so as to identify potential aneurysms 508 within the virtual skeleton model 400. In certain embodiments, the one or more filtering steps are based on one or more of the statistics determined by the construction model 106. In certain embodiments, the filtering module 108 filters the virtual skeleton model 400 based on one or more statistics for each of the one or more predefined geometric shapes fitted along each edge 310. In certain embodiments, the one or more statistics include the mean, minimum, maximum, and standard deviations for each of the one or more predefined geometric shapes. In certain embodiments, one or more of the steps 1412 within the one or more filtering steps are repeated or iterated to further identify additional potential aneurysms 508 in the virtual skeleton model 400.

In certain embodiments, the one or more filtering steps 1412 include a step based on ellipse area statistics. In certain embodiments, the one or more filtering steps 1412 include a step based on ellipse eccentricity statistics. Filtering based on ellipse eccentricity may identify a region of the virtual skeleton model 400 as a potential aneurysm 508.

In certain embodiments, the filtering module 108 flags skeleton points 406 within the virtual skeleton model 400 as potential aneurysm 508 and then removes the flagged skeleton points 406 from the virtual skeleton module 400 based on a comparison of the eccentricity calculated for the ellipse 602 and an eccentricity threshold value.

The method continues to step 1414 where the filtering module 108 determines one or more volumes related to the potential aneurysm 508. In certain embodiments, the filtering module 108 compares the volume of a healthy vessel in the region of the potential aneurysms 508 with the volume of the potential aneurysms 508.

In certain embodiments, the filtering module 108 computes a cylindrical volume using the ellipse areas in the region of the potential aneurysm 508 to represent the volume 704 of the potential aneurysm 508. In certain embodiments, the filtering module 108 computes a cylindrical volume in the region of the potential aneurysm 508 by interpolating the areas of the ellipses on the sides of the potential aneurysm 508 into the region of the potential aneurysm 508. In this way, the interpolated volume 702 represents the virtual volume of a healthy vessel in the area of the potential aneurysm 508.

The comparison between the volumes 702, 704 indicates whether the potential aneurysm 508 is a true positive 900 or is a false positive 902. In certain embodiments, if the volume of the potential aneurysm 508 is less than 1.1*the virtual volume of the healthy vessel 702 in the region of the potential aneurysm 508 then the potential aneurysm 508 is a false positive 902.

The method continues to step 1416 where the identified potential aneurysms 508, 704 are shown in the display device 112 for final selection by the healthcare provider. At step 1418, the healthcare provider screens out false positives 902 from the list of potential aneurysms 508, 704 using the user input 114. In certain embodiments, there are no more than a few false positives 902 per case and those false positives 902 are easily screened out by the healthcare provider via the display device 112. In certain embodiments, the user input 114 allows the healthcare provider to adjust the type of aneurysm (fusiform 1010 or saccular 1000) for the aneurysms selected.

Figure 15:
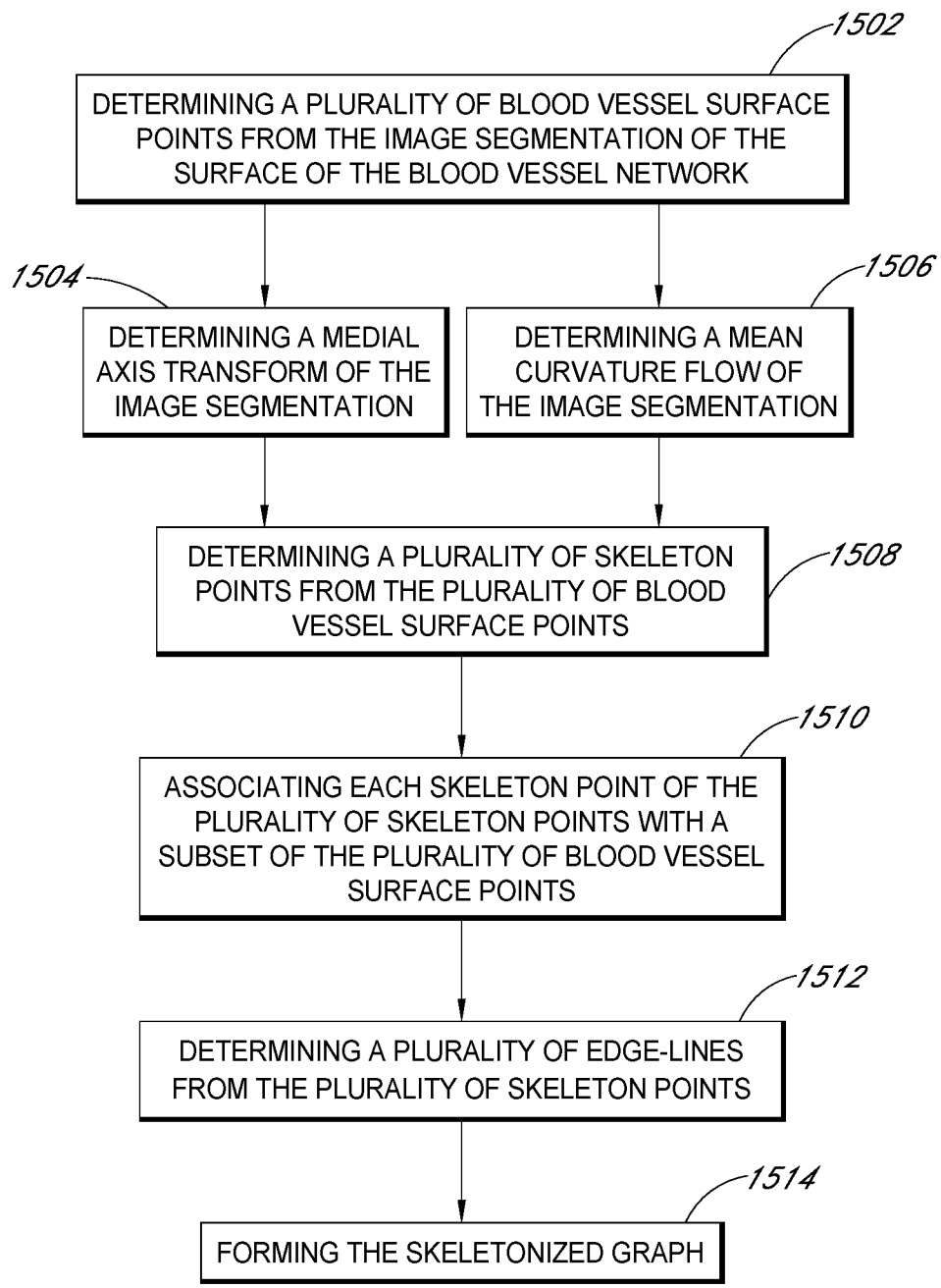
FIG. 15 illustrates a method performed by the skeletonization model for forming a skeletonized graph or virtual skeleton model.

FIG. 15 illustrates a method performed by the skeletonization model 102 for forming a skeletonized graph or virtual skeleton model 400. In certain embodiments, the skeletonization module 102 employs a mean curvature method 410 for creating the virtual skeleton model 400. In certain embodiments, the mean curvature method 410 comprises a single method or algorithm or a combination of more than one method or algorithm. In embodiments comprising more than one method, the methods may be employed in series in certain embodiments, in parallel in certain embodiments, concurrently or overlapping in duration in certain embodiments, and simultaneously in certain embodiments. For example, the first method and the second method may be employed simultaneously to create the virtual skeleton model 400.

In certain embodiments, the mean curvature method 410 comprises a first method and a second method. In certain embodiments, the first method is a medial axis method and the second method is a mean curvature flow method.

The method begins at step 1502 where the skeletonization module 102 determines a plurality of blood vessel surface points 408 from the image segmentation of the surface of the blood vessel network 402. The method continues to steps 1504 and 1506 where the skeletonization module 102 determines a medial axial transform of the image segmentation and a mean curvature flow of the image segmentation, respectively.

In certain embodiments, steps 1504 and 1506 are employed in series, in parallel, concurrently or overlapping in duration, or simultaneously. For example, steps 1504 and 1506 may be employed simultaneously.

The method continues to step 1508 where the skeletonization module 102 determines a plurality of skeleton points 406 from the plurality of blood vessel surface points 408. The method continues to step 1510 where the skeletonization module 102 associates each skeleton point 406 of the plurality of skeleton points 406 with a subset of the plurality of blood vessel surface points 408. The method continues to step 1512 where the skeletonization module 102 determines a plurality of edge-lines 310 from the plurality of skeleton points 406. The method continues to step 1514 where the skeletonization module 102 forms the skeletonized graph or virtual skeleton model 400.

Figure 16:
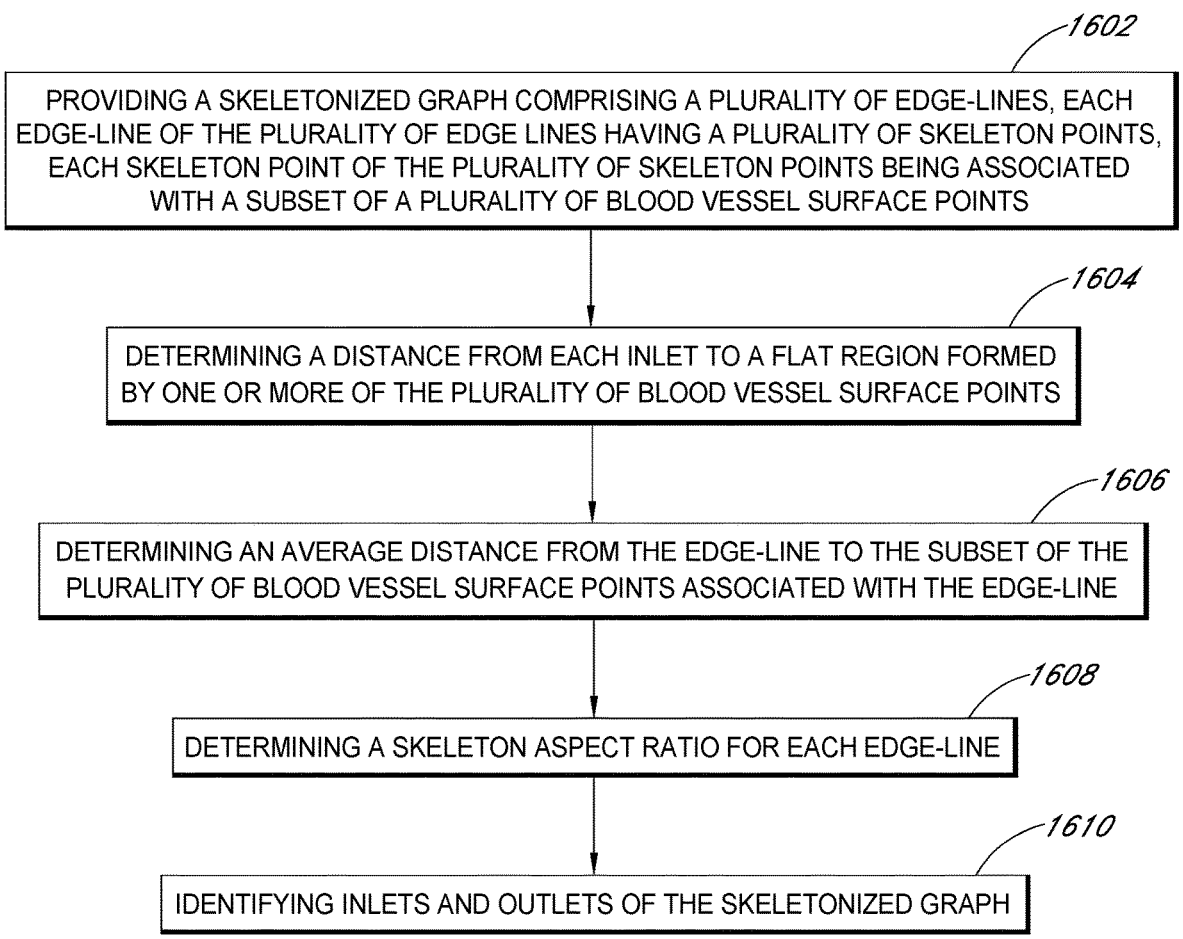
FIG. 16 illustrates a method performed by the inlet/outlet module to identify inlets points and outlets points of the skeletonized graph or virtual skeleton model.

FIG. 16 illustrates a method performed by the inlet/outlet module 104 to identify inlets points 502 and outlets points 504 of the skeletonized graph or virtual skeleton model 400. The method begins at step 1602 where the skeletonized graph or virtual skeleton model 400 is provided to the inlet/outlet module 104. In certain embodiments, the virtual skeleton model 400 comprises a plurality of edge 310. Each edge 310 has a plurality of skeleton points 406. Each skeleton point 406 is associated with a subset of a plurality of blood vessel surface points 408. The method continues to step 1604 where the inlet/outlet module 104 determines a distance from each inlet 502 to a flat region formed by one or more of the plurality of blood vessel surface points 408. The method continues to step 1606 where the inlet/outlet module 104 determines an average distance from the edge 310 to the subset of the plurality of blood vessel surface points 408 associated with the edge 310. The method continues to step 1608 where the inlet/outlet module 104 determines a skeleton aspect ratio for each edge 310. The method continues to step 1610 where the inlet/outlet module 104 identifies inlets 502 and outlets 504 of the skeletonized graph or virtual skeleton model 400.

Figure 17:
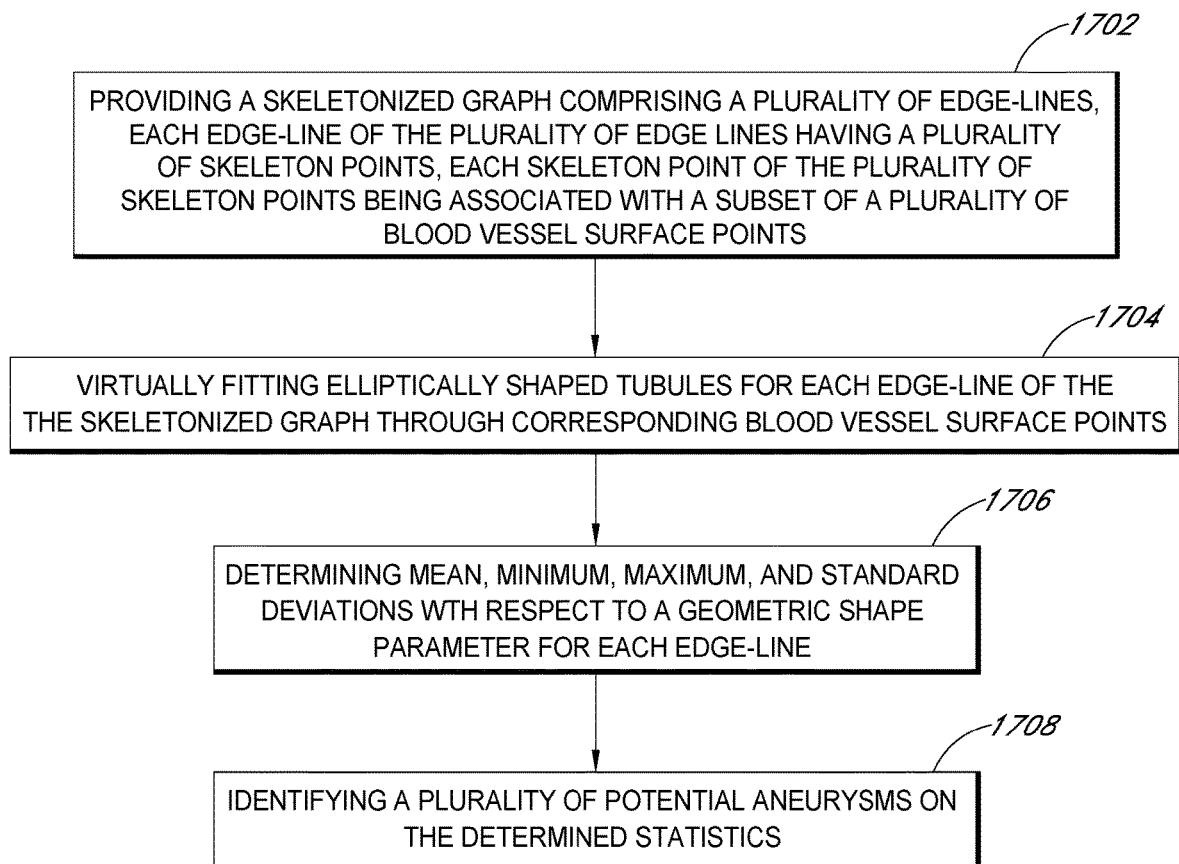
FIG. 17 illustrates a method performed by the construction module to identify potential aneurysm.

FIG. 17 illustrates a method performed by the construction module 106 to identify potential aneurysm 508. The method begins at step 1702 where the construction module 106 is provided with a skeletonized graph or virtual skeleton model 400. In certain embodiments, the virtual skeleton model 400 comprises a plurality of edge 310. Each edge 310 has a plurality of skeleton points 406. Each skeleton point 406 is associated with a subset of a plurality of blood vessel surface points 408. The method continues to step 1704 where the construction module 106 virtually fits ellipses 602 to form elliptically shaped tubules 606 for each edge 310 of the skeletonized graph or virtual skeleton model 400 through corresponding blood vessel surface points 408. The method continues to step 1706 where the construction module 106 determines mean, minimum, maximum, and standard deviations for the geometric parameters for each edge 310. The method continuous to step 1708 where the construction module 106 identifies a plurality of potential aneurysms 508 based on the determined statistics.

Figure 18:
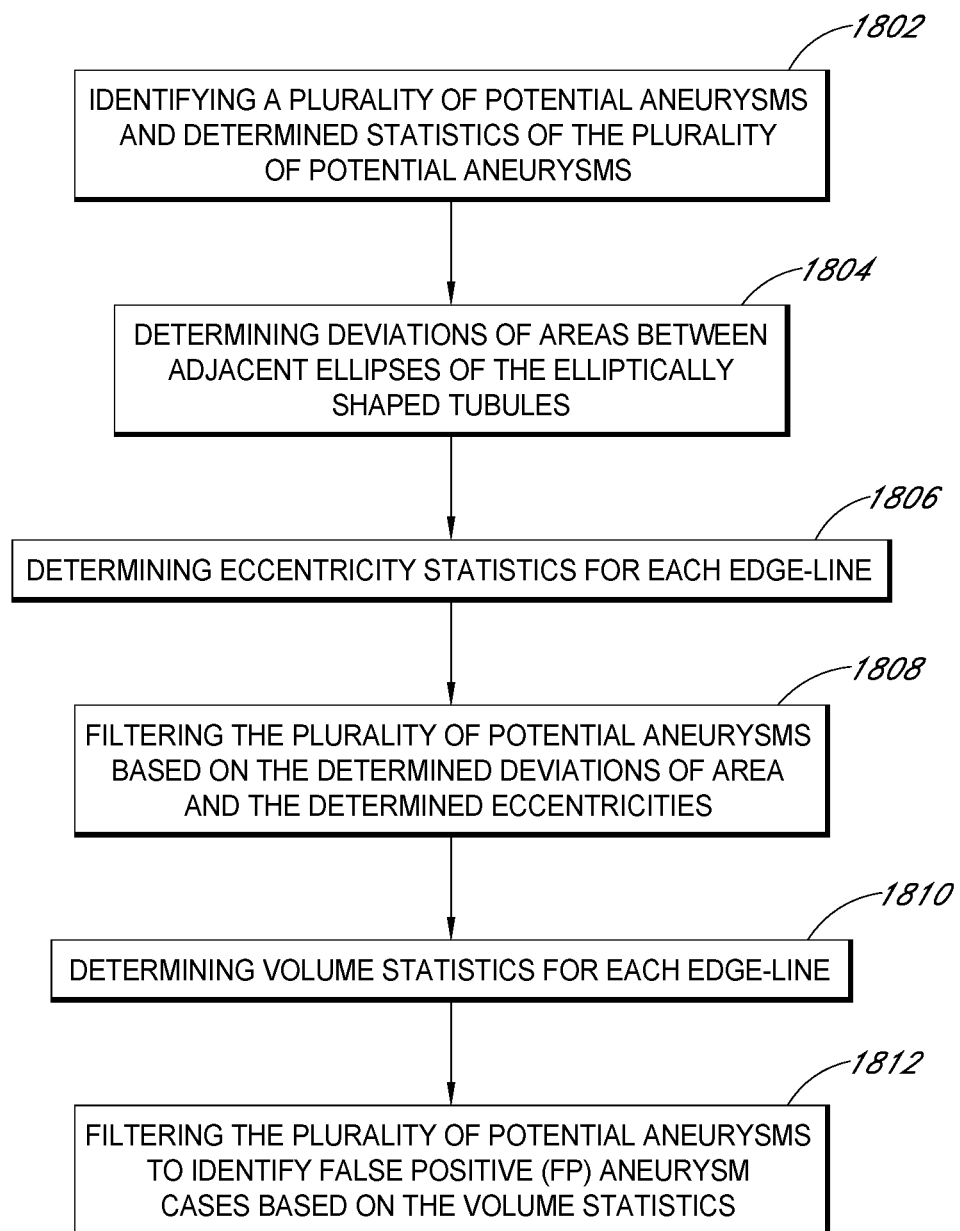
FIG. 18 illustrates a method performed by the filtering module to filter potential aneurysm identified by the construction module.

FIG. 18 illustrates a method performed by the filtering module 108 to filter potential aneurysms 508 identified by the construction module 106. The method begins at step 1802 where the filtering module 108 identifies a plurality of potential aneurysms 508 and determined statistics of the plurality of potential aneurysms 508. The method continues to step 1804 where the filtering module 108 determines deviations of areas between adjacent ellipses 602 of the elliptically shaped tubules 606. The method continues to step 1806 where the filtering module 108 determines eccentricity statistics for each ellipse 602 along the edge 310. The method continues to step 1808 where the filtering module 108 filters the plurality of potential aneurysms 508 based on the determined deviations of area and the determined eccentricities. The method continues to step 1810 where the filtering module 108 determines volume statistics for each ellipse 602 along the edge 310. The method continues to step 1812 where the filtering module 108 filters the plurality of potential aneurysms 508 to identify false positives (FP) aneurysm cases based on the determined volume statistics.

Figure 19:
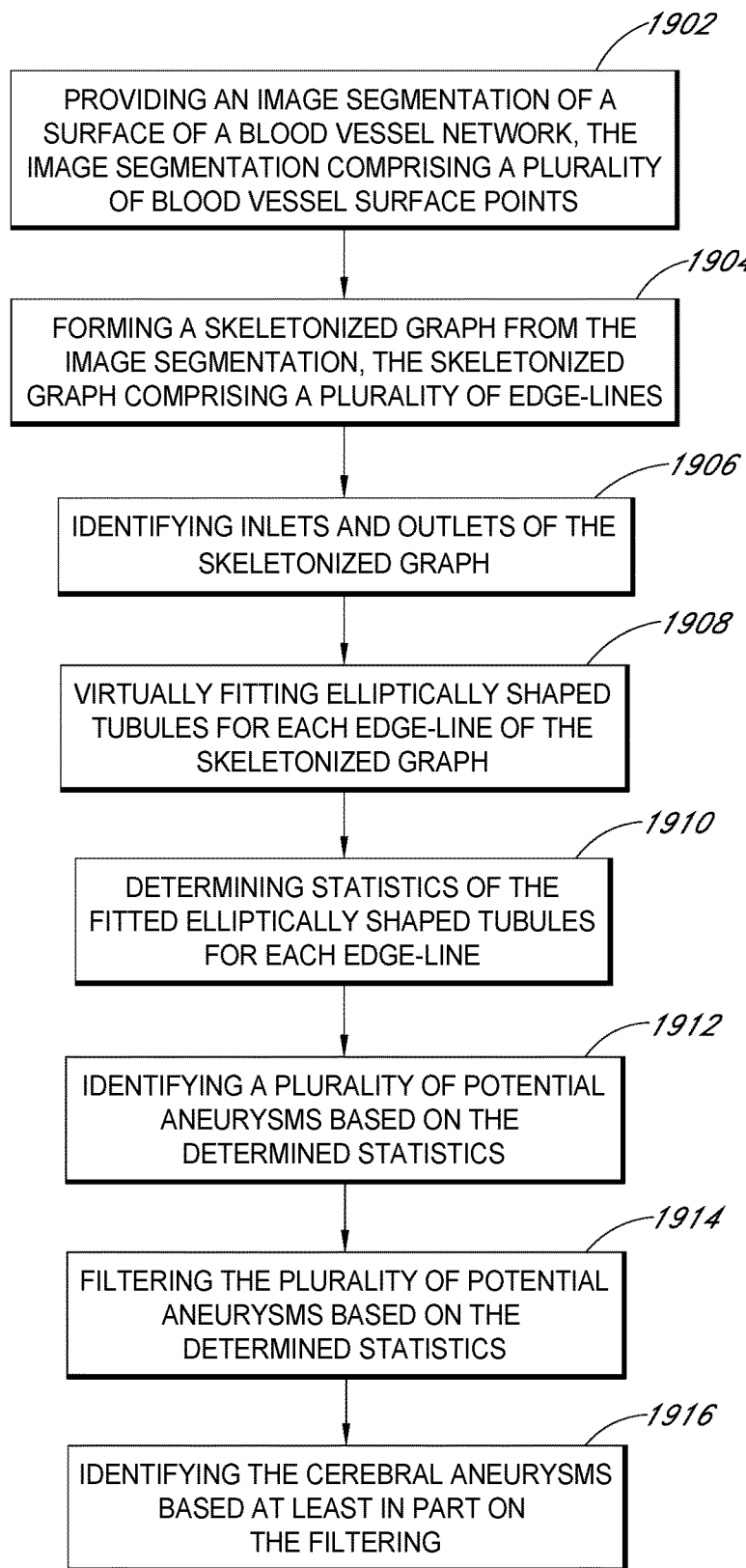
FIG. 19 illustrates a method of identifying a cerebral aneurysm from an image segmentation.

FIG. 19 illustrates a method of identifying a cerebral aneurysm from an image segmentation. In certain embodiments, the method is performed by the computer system 100 illustrated in FIG. 1. The process begins at step 1902 with providing an image segmentation of a surface of a blood vessel network 402. The image segmentation comprises a plurality of blood vessel surface points 408. The method continuous to step 1904 with forming a skeletonized graph or virtual skeleton model 400 from the image segmentation. The skeletonized graph or virtual skeleton model 400 comprises a plurality of edge 310. The method continues to step 1906 with identifying inlets 502 and outlets 504 of the skeletonized graph or virtual skeleton model 400. The method continues to step 1908 with virtually fitting elliptically shaped tubules 606 comprising ellipses 602 for each edge 310 of the skeletonized graph or virtual skeleton model 400. The method continues to step 1910 with determining statistics of the fitted elliptically shaped tubules for each edge 310. The method continues to step 1912 with identifying a plurality of potential aneurysms 508 based on the determined statistics. The method continues to step 1914 with filtering the plurality of potential aneurysms 508 based on the determined statistics. The method continues to step 1916 with identifying the cerebral aneurysms based at least in part on the filtering.

Figure 20:
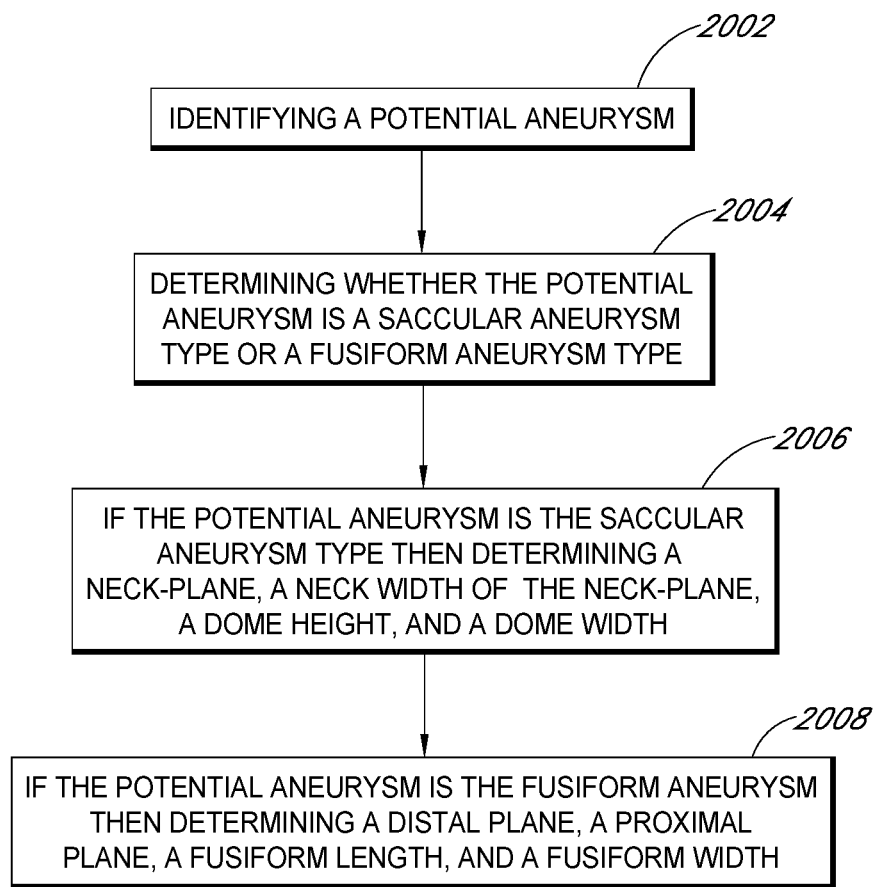
FIG. 20 illustrates a method of measuring a cerebral aneurysm depending on whether the aneurysm is a saccular or fusiform aneurysm.

FIG. 20 illustrates a method of measuring a cerebral aneurysm depending on whether the aneurysm is a saccular or fusiform aneurysm. The method begins at step 2002 where the filtering module 108 identifies a potential aneurysm 508. The method continues to step 2004 where the filtering module 108 determines whether the potential aneurysm 508 is a saccular aneurysm type or a fusiform aneurism type. The method continues to step 2006 where the filtering module 108 determines a neck plane 1006, a neck width 1008 of the neck plane 1006, a dome height 1004, and dome width 1002 of the potential aneurysm 508 if it is a saccular aneurysm. The method continues to step 2008 where the filtering module 108 determines a distal plane 1016, a proximal plane 1018, a fusiform length 1014, and a fusiform width 1012 of the potential aneurysm 508 if it is a fusiform aneurysm.

FIG. 21 illustrates a method for comparing geometry of a cerebral aneurysm over a period of time. The method begins at step 2102 with providing a first image segmentation of a surface of a blood vessel network 402. The method continues to step 2104 with forming a first skeletonized graph from the first image segmentation. The first skeletonized graph comprises a plurality of edges 310. The method continues to step 2106 with identifying one or more first nodes within the first skeletonized graph or virtual skeleton model 400. Each of the one or more first nodes intersecting more than two edges 310 of the plurality of edge 310. The method continues to step 2108 with identifying one or more first terminal points within the first skeletonized graph. Each of the one or more first terminal points intersecting only one edge 310 of the plurality of edges 310. The method continues to step 2110 with providing a second image segmentation of a surface of the blood vessel network 402. The method continues to step 2112 with forming a second skeletonized graph from the second image segmentation. The second skeletonized graph comprises a plurality of edges 310. The method continues to step 2114 with identifying one or more second nodes within the second skeletonized graph or virtual skeleton model 400. Each of the one or more second nodes intersecting more than two edges 310 of the plurality of edge 310. The method continues to step 2116 with identifying one or more second terminal points within the second skeletonized graph. Each of the one or more second terminal points intersecting only one edge 310 of the plurality of edges 310. The method continues to step 2118 with overlapping the first skeletonized graph and the second skeletonized graph by orienting the one or more first nodes with the one or more second nodes and orienting the one or more first terminal points with the one or more second terminal points. The method continues to step 2120 with comparing the geometry of the cerebral aneurysm when the first skeletonized graph is overlapped with the second skeletonized graph.

Advantages of certain embodiments disclosed herein include automatically identify the aneurysm; using statistics to pare down to the healthy anatomy and so automatically define thresholds which could be generalized for other regions of the anatomy; and using statistical filtering to identify abnormalities in the vasculature.

In certain embodiments, the disclosed invention is related to CAD (Computer Aided Detection) method for cerebral aneurysm detection/analysis and measurement. Major features, that each in itself and all together, comprise the novelty of the method compared to prior art include (1) skeletonization based on the "Mean Curvature Skeleton" for the entire blood vessel network from the segmented image. Although previous arts in the field used center line computation, with the employment of the MAT only (medial axis transform and its derivative), usually the purpose of center lines was to represent "healthy" vessels where big aneurysms were pre-screened out already. In the presented disclosure a combination of MAT and Curvature Flow "Mean Curvature Skeleton" is employed to capture the topology and major geometry of the whole vessel network, excluding noises, in the segmented images; (2) identifying inlets/outlets of the vasculature by using skeleton information obtained in step 1, all possible inlets/outlets are identified automatically and presented for final approval/adjustment by the user; (3) construct elliptically shaped tubules for each edge; (4) compute statistics of fitted ellipse parameters for each edge-line; (5) perform iterative filtering of aneurysm based on ellipse area statistics for each edge-line; (6) perform filtering of aneurysm based on ellipse eccentricity statistics for each edge-line; and (7) filter out false positive (FP) aneurysm cases by volumetric ellipse tubules filtering. Steps (3)-(7) are based on using fitted ellipses as the "cross sectional" shape of the blood vessel. Prior art has not fitted ellipses in a consistent and systematic way to detect the aneurysm itself. Also the "cross-section" points in certain embodiments are at each centerline point, not the geometric cross section, but the set of points that collapsed to that skeleton point.

In certain embodiments of the aneurysm measurement, the automatic identification of the separation plane (for saccular form aneurysm), utilizing points weighted by negative surface Gaussian curvature values ("neck points") is advantageous. In certain embodiments for aneurysm comparison, the use of the skeleton features to orient multiple geometries with respect to each other is advantageous. This allows for automatic tracking and comparison of aneurysms over time.

The terms "processor", as used herein is a broad term, and is to be given its ordinary and customary meaning to a person of ordinary skill in the art (and is not to be limited to a special or customized meaning), and refer without limitation to a computer system, state machine, processor, or the like designed to perform arithmetic or logic operations using logic circuitry that responds to and processes the basic instructions that drive a computer. In some embodiments, the terms can include ROM and/or RAM associated therewith.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical steps, blocks, modules and circuits described in connection with the present disclosure (such as the steps of FIGS. 1 and 9) may be implemented or performed with a general purpose processor, GPU computational units (using CUDA or OpenCL), or part of the computation may be performed on a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by an electronic communication device as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that an electronic communication device can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Headings are included herein for reference and to aid in locating various sections. These headings are not intended to limit the scope of the concepts described with respect thereto. Such concepts may have applicability throughout the entire specification.

The foregoing illustrated embodiments have been provided solely for illustrating the functional principles of the present invention and are not intended to be limiting. For example, the present invention may be practiced using different overall structural configuration and materials. Persons skilled in the art will appreciate that modifications and alterations of the embodiments described herein can be made without departing from the spirit, principles, or scope of the present invention. The present invention is intended to encompass all modifications, substitutions, alterations, and equivalents within the spirit and scope of the following appended claims.

What is claimed is:

1. A method for detecting an aneurysm, the method comprising:
   providing an image segmentation of a surface of a blood vessel network, the image segmentation comprising a plurality of blood vessel surface points;
   forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;

identifying inlets and outlets of the virtual skeleton model;
virtually fitting elliptically shaped tubules for each edge of the skeletonized graph;
determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein forming the virtual skeleton model comprises simultaneously determining a medial axis transform of the image segmentation and a mean curvature flow of the image segmentation.

2. The method of claim 1, wherein forming the virtual skeleton model comprises determining a medial axis transform of the image segmentation.

3. The method of claim 1, wherein identifying the inlets of the virtual skeleton model is based at least in part on determining a distance from each inlet to a flat region formed by one or more of the plurality of blood vessel surface points.

4. The method of claim 1, wherein identifying the inlets of the virtual skeleton model is based at least in part on an average distance from each edge to the subset of the plurality of blood vessel surface points associated with the edge.

5. The method of claim 1, wherein virtually fitting elliptically shaped tubules for each edge of the virtual skeleton model is performed at each skeleton point of the plurality of skeleton points associated with the edge.

6. The method of claim 1, wherein determining statistics of the fitted elliptically shaped tubules for each edge comprises one or more of a mean, minimum, maximum, and standard deviations.

7. The method of claim 1, wherein determining statistics of the fitted elliptically shaped tubules comprises area statistics for each edge.

8. A system for aneurysm detection and analysis, the system comprising:
one or more processors configured to:
provide an image segmentation of a surface of a blood vessel network, the image segmentation comprising a plurality of blood vessel surface points;
form a virtual skeleton model from the image segmentation, the virtual skeleton model comprising a plurality of edges, each edge of the plurality of edge lines having a plurality of skeleton points, each skeleton point of the plurality of skeleton points being associated with a subset of the plurality of blood vessel surface points;
virtually fit elliptically shaped tubules for each edge of the virtual skeleton model; and
identify the aneurysm based at least in part on the virtually fit elliptically shaped tubules,
wherein the one or more processors determine a mean curvature flow of the image segmentation to form the virtual skeleton model.

9. The system of claim 8, wherein the one or more processors is further configured to determine statistics of the fitted elliptically shaped tubules for each edge.

10. The system of claim 9, wherein the one or more processors is further configured to identify a plurality of potential aneurysms based on the determined statistics.

11. The system of claim 10, wherein the one or more processors is further configured to filter the plurality of potential aneurysms based on the determined statistics.

12. The system of claim 11, wherein the one or more processors is further configured to identify the aneurysm based at least in part on the filtering.

13. The system of claim 8, wherein the one or more processors is further configured to identify inlets and outlets of the skeletonized graph.

14. A method for detecting an aneurysm, the method comprising:
providing an image segmentation of a surface of a blood vessel network, the image segmentation comprising a plurality of blood vessel surface points;
forming a virtual skeleton model comprising a plurality of edges, each edge of the plurality of edges having a plurality of skeleton points, each skeleton point of the plurality of skeleton points being associated with a subset of the plurality of blood vessel surface points;
virtually fitting elliptically shaped tubules for each edge of the virtual skeleton model; and
identifying a potential aneurysm based on the fitted elliptically shaped tubules,
wherein forming the virtual skeleton model comprises determining a mean curvature flow of the image segmentation.

15. A method for detecting an aneurysm, the method comprising:
providing an image segmentation of a surface of a blood vessel network, the image segmentation comprising a plurality of blood vessel surface points;
forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;
identifying inlets and outlets of the virtual skeleton model;
virtually fitting elliptically shaped tubules for each edge of the skeletonized graph;
determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein forming the virtual skeleton model comprises determining a mean curvature flow of the image segmentation.

16. A method for detecting an aneurysm, the method comprising:
providing an image segmentation of a surface of a blood vessel network, the image segmentation comprising a plurality of blood vessel surface points;
forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;
identifying inlets and outlets of the virtual skeleton model;
virtually fitting elliptically shaped tubules for each edge of the skeletonized graph;

determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein identifying the outlets of the virtual skeleton model is based at least in part on a skeleton aspect ratio for each edge.

17. A method for detecting an aneurysm, the method comprising:
providing an image segmentation of a surface of a blood vessel network, the image segmentation comprising a plurality of blood vessel surface points;
forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;
identifying inlets and outlets of the virtual skeleton model;
virtually fitting elliptically shaped tubules for each edge of the skeletonized graph;
determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein filtering the plurality of potential aneurysms based on the determined statistics comprises determining deviations of areas between adjacent ellipses of the elliptically shaped tubules.

18. A method for detecting an aneurysm, the method comprising:
providing an image segmentation of a surface of a blood vessel network, the image segmentation comprising a plurality of blood vessel surface points;
forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;
identifying inlets and outlets of the virtual skeleton model;
virtually fitting elliptically shaped tubules for each edge of the skeletonized graph;
determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein determining statistics of the fitted elliptically shaped tubules comprises eccentricity statistics for each edge.

19. A method for detecting an aneurysm, the method comprising:
providing an image segmentation of a surface of a blood vessel network, the image segmentation comprising a plurality of blood vessel surface points;
forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;
identifying inlets and outlets of the virtual skeleton model;
virtually fitting elliptically shaped tubules for each edge of the skeletonized graph;
determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein filtering the plurality of potential aneurysms based on the determined statistics comprises determining deviations of eccentricities between adjacent ellipses of the elliptically shaped tubules.

20. A method for detecting an aneurysm, the method comprising:
providing an image segmentation of a surface of a blood vessel network, the image segmentation comprising a plurality of blood vessel surface points;
forming a virtual skeleton model from the image segmentation, the virtual skeleton model comprising a plurality of edges, each edge of the plurality of edges having a plurality of skeleton points, each skeleton point of the plurality of skeleton points being associated with a subset of the plurality of blood vessel surface points;
identifying inlets and outlets of the virtual skeleton model;
virtually fitting elliptically shaped tubules for each edge of the skeletonized graph;
determine statistics of the fitted elliptically shaped tubules for each edge;
identifying a plurality of potential aneurysms based on the determined statistics;
filtering the plurality of potential aneurysms based on the determined statistics; and
identifying the aneurysm based at least in part on the filtering,
wherein determining statistics of the fitted elliptically shaped tubules comprises volume statistics for each edge, and further comprising filtering the plurality of potential aneurysms to identify false positive (FP) aneurysm cases based on the volume statistics.

* * * * *